US012636249B2

(12) United States Patent (10) Patent No.: US 12,636,249 B2
Genosar et al. (45) Date of Patent: *May 26, 2026

(54) CONCENTRATED INJECTABLE TRANEXAMIC ACID COMPOSITIONS AND METHODS OF USE THEREOF

(71) Applicant: Galen Limited, Craigavon (GB)

(72) Inventors: Amir Genosar, Broomfield, CO (US); Xicheng Sun, Broomfield, CO (US); Melissa Varner, Broomfield, CO (US)

(73) Assignee: Galen Limited, Craigavon (GB)

( * ) Notice: Subject to any disclaimer, the term of this patent is extended or adjusted under 35 U.S.C. 154(b) by 0 days.

This patent is subject to a terminal disclaimer.

(21) Appl. No.: 19/366,287

(22) Filed: Oct. 22, 2025

(65) Prior Publication Data

US 2026/0048004 A1 Feb. 19, 2026

Related U.S. Application Data

(63) Continuation of application No. 18/107,421, filed on Feb. 8, 2023.

(60) Provisional application No. 63/340,298, filed on May 10, 2022, provisional application No. 63/308,367, filed on Feb. 9, 2022.

(51) Int. Cl.
*A61K 9/00* (2006.01)
*A61K 31/045* (2006.01)
*A61K 31/195* (2006.01)
*A61K 47/02* (2006.01)
*A61K 47/10* (2017.01)
*A61K 47/54* (2017.01)
*A61P 7/04* (2006.01)

(52) U.S. Cl.
CPC .......... *A61K 9/0019* (2013.01); *A61K 31/045* (2013.01); *A61K 31/195* (2013.01); *A61K 47/02* (2013.01); *A61K 47/10* (2013.01); *A61K 47/542* (2017.08); *A61P 7/04* (2018.01)

(58) Field of Classification Search
CPC .. A61K 9/0019; A61K 31/045; A61K 31/195; A61K 47/02; A61K 47/10; A61K 47/542; A61P 7/04
See application file for complete search history.

(56) References Cited

U.S. PATENT DOCUMENTS 4,377,572 A 3/1983 Schwarz et al.
9,301,936 B2 4/2016 Buderer et al.
(Continued)

FOREIGN PATENT DOCUMENTS

CN 106109401 11/2016
JP 2011-195460 10/2011
(Continued)

OTHER PUBLICATIONS

<71> Sterility Tests, USP-NF, 8 pages (Downloaded 2020).
(Continued)

*Primary Examiner* — Deborah D Carr
(74) *Attorney, Agent, or Firm* — Brian E. Davy; Bozicevic, Field & Francis LLP

(57) ABSTRACT

Concentrated tranexamic acid compositions suitable for intramuscular administration via auto-injector are provided. Methods of treating non-compressible hemorrhage are also provided. Kits and auto-injectors comprising the tranexamic acid compositions are further provided.

20 Claims, 7 Drawing Sheets

(56) References Cited

U.S. PATENT DOCUMENTS

| | | | |
|---|---|---|---|
| 9,820,913 | B2 | 11/2017 | Genosar |
| 10,028,886 | B2 | 7/2018 | Genosar |
| 10,716,901 | B2 | 7/2020 | Genosar |
| 10,864,139 | B2 | 12/2020 | Genosar |
| 10,980,757 | B2 | 4/2021 | Jacobsen et al. |
| 10,981,713 | B2 | 4/2021 | Genosar |
| 11,001,435 | B2 | 5/2021 | Genosar |
| 11,654,057 | B2 * | 5/2023 | Manasco .............. A61K 31/197 |
| | | | 604/290 |
| 2011/0159073 | A1 | 6/2011 | deJuan et al. |
| 2013/0142844 | A1 | 6/2013 | Hamby et al. |
| 2015/0051580 | A1 | 2/2015 | Shain |
| 2016/0206580 | A1 | 7/2016 | Los et al. |
| 2017/0360705 | A1 | 12/2017 | Tamarkin et al. |
| 2019/0224121 | A1 | 7/2019 | Erstad et al. |
| 2020/0046663 | A1 | 2/2020 | Murdock et al. |
| 2020/0078326 | A1 * | 3/2020 | Jacobsen .............. A61K 9/0019 |
| 2020/0323837 | A1 | 10/2020 | Murdock et al. |
| 2020/0345937 | A1 | 11/2020 | Genosar |
| 2021/0205246 | A1 | 7/2021 | Jacobsen |

FOREIGN PATENT DOCUMENTS

| | | | |
|---|---|---|---|
| JP | | 6148454 | 6/2017 |
| UA | | 142859 | 6/2020 |
| WO | WO 2015006299 | | 1/2015 |
| WO | WO 2016118652 | | 7/2016 |
| WO | WO 2018187470 | | 10/2018 |
| WO | WO 2019007469 | | 1/2019 |
| WO | WO-2019007469 | A1 * | 1/2019 ........... A61L 24/108 |
| WO | WO 2019045989 | | 3/2019 |

OTHER PUBLICATIONS

<85> Bacterial Endotoxins Test, Stage 6 Harmonization, pp. 1-5 (Official Dec. 1, 2012).

Abdolrazaghnejad et al., "Pain Management in the Emergency Department: a Review Article on Options and Methods." Adv J Emergency Medicine, 2(4):e45, pp. 1-14 (2018).

Bakke et al., "Intramuscular uptake of tranexamic acid during haemorrhagic shock in a swine model," Scand J Trauma Resusc Emerg Med, vol. 29, Article No. 171, https://doi.org/10.1186/s13049-021-00983-2 (2021).

"Benzyl Alcohol" in Handbook of Pharmaceutical Excipients 2009, 6th Edition, Crowe, Sheskey and Quinn Ed. (Year: 2009).

Butala et al., "Medication error: Subarachnoid injection of tranexamic acid," Indian Journal of Anaesthesia, vol. 56, Issue 2, pp. 168-170 (Mar.-Apr. 2012).

Center for Drug Evaluation and Research {GOER) and Center for Veterinary Medicine {CVM), "Guidance for Industry for the Submission Documentation for Sterilization Process Validation in Applications for Human and Veterinary Drug Products", 23 pages {Nov. 1994).

Chiang et al., "Prehospital intravenous epinephrine may boost survival of patients with traumatic cardiac arrest: a retrospective cohort study," Scandinavian Journal of Trauma, Resuscitation and Emergency Medicine. 23:102 DOI 10.1186/s13049-015-0181-4, pp. 1-7 (2015).

Cyklokapron Prescribing Information, Pfizer Labs, 10 pages (Mar. 2021).

Cyklokapron Prescribing Information, Pfizer, 6 pages (Dec. 2014).

Donnelly, "Stability of Tranexamic Acid Mouth Rinse," International Journal of Pharmaceutical Compounding, vol. 22, No. 5, pp. 412-416 (Sep./Oct. 2018).

Fauzi et al., "Compared to Conventional Dressing Techniques, Tranexamic Acid Injection Provide Beller Surgical Outcomes in Spinal Fusion Surgery," Biomedical & Pharmacology Journal, vol. 11, No. 4, pp. 2215-2220 (Dec. 2018).

Grassin-Delyle et al., "Pharmacokinetics of intramuscular tranexamic acid in bleeding trauma patients: a clinical trial," British Journal of Anaesthesia, vol. 126, No. 1, pp. 201-209 (2021).

Grzelecki et al., Efficacy of intravenous tranexamic acid administration in revision hip arthroplasty. Orthopade, vol. 50, pp. 464-470, https://doi.org/10.1007/s00132-020-03959-9 (Jun. 2021).

Hopkins et al., "Large-volume IM injections: A review of best practices," Oncology Nurse Advisor, pp. 32-37 {Jan./Feb. 2013).

International Search Report and Written Opinion for Application No. PCT/US23/62217 mailed Jun. 14, 2023.

Kane et al., "Physiologically based modelling of tranexamic acid pharmacokinetics following intravenous, Intramuscular, subcutaneous and oral administration in healthy volunteers," European Journal of Pharmaceutical Sciences, 164:105893, pp. 1-10 (Jun. 2021).

Kang et al., "Effect of Multiple Doses of Intravenous Tranexamic Acid on Perioperative Blood Loss in Total Knee Arthroplasty: A Randomized Controlled Study," Orthopaedic Surgery, vol. 13, No. 1, pp. 126-133, DOI: 10.1111/os.12850 (2021).

Lecker et al. (2012) "Tranexamic acid concentrations associated with human seizures inhibit glycine receptors" The J. of Clinical Investigation, 122(12)4654-4666.

PH Measurement per USP <791> Preparing your Lab, Thermo Scientific, R-USP791-E 0815 RevB, 13 pages (2015).

Picetti et al., What concentration of tranexamic acid is needed to inhibit fibrinolysis? A systematic review of pharmacodynamics studies, Blood Coagulation and Fibrinolysis, vol. 30, No. 1, pp. 1-10 (2019).

Saki et al., "Intralesional transexamic acid as an effective treatment for repigmentation after depigmentation therapy with monobenzyl ether of hydroquinone: a case report," Iranian Journal of Dermatology, vol. 22, No. 2, pp. 79-81 (2019).

Scavone et al., "Efficacy and Safety Profile of Diclofenac/Cyclodextrin and Progesterone/Cyclodextrin Formulations: A Review of the Literature Data," Drugs RD, vol. 16, pp. 129-140 (2016).

Sheng et al. "The Biopharmaceutics Classification System" in Oral Drug Absorption, CRC Press, 2010. pp. 132-154. (Year: 2010).

Spruce et al., "Pharmacokinetics of Tranexamic Acid Given as an Intramuscular Injection Compared to Intravenous Infusion in a Swine Model of Ongoing Hemorrhage," Shock, vol. 53, No. 6, pp. 754-760 (2020).

The Merck Index, 9390. Tranexamic Acid, pp. 1368-1369, 10th Edition (1983).

Third Party Observation for Application No. PCT/US2023/062217 mailed Feb. 16, 2024.

Tranexamic Acid European Pharmacopoeia 7.0, pp. 3122-3123 (2008).

Tranexamic Acid in Sodium Chloride Injection Prescribing Information, Exela Pharma Sciences, LLC, 8 pages (Apr. 2019).

Tranexamic Acid Injection BP 250mg, Centurion Healthcare Private Limited, 2 pages (Copyright 2019).

Tranexamic Acid, Caspian Tamin Pharmaceutical Co., 3 pages (Downloaded 2021).

Tseng et al., "Solubilities of amino acids in water at various pH values under 298.15 K," Fluid Phase Equilibria, vol. 285, pp. 90-95 (2009).

Water for injections, European Pharmacopoeia, Eleventh Edition, Supplement 11.1, Apr. 2023:0169, pp. 4773-4775.

Wilson et al., Benzyl Alcohol as Alternative Local Anesthetic, Annals of Emergency Medicine, vol. 33, No. 5, pp. 495-499 (May 1999).

Wright, "Battlefield administration of tranexamic acid by combat troops: a feasibility analysis," Journal of the Royal Army Medical Corps, vol. 160, No. 4, pp. 271-272 (Dec. 2014).

Extended European Search Report dated Feb. 24, 2026, Appln. No. EP 23753623.0, 9 pages.

Chang et al. (2022) "Effect of Sequential Intravenous and Oral Tranexamic Acid on Hemoglobin Drop After Total Knee Arthroplasty" J Bone Joint Surg Am., 104:154-159.

Charoencholvanich et al. (2011) "Tranexamic Acid Reduces Blood Loss and Blood Transfusion after TKA" Clin Orthop Relat Res., 469:2874-2880.

FDA Details of Transamin® Injection Products (2026) 2 pages.

Marketing Authorization—Transamin®, No. 1A 515/46 (2003) 3 pages.

(56) References Cited

OTHER PUBLICATIONS

NIH National Library of Medicine: Clinical Trials.gov, "Serial Use of Intravenous and Oral Tranexamic Acid in Primary Total Knee Arthroplasty Patients" (Retrieved from the internet on Dec. 23, 2025. Retrieved from:<URL: https://clinicaltrials.gov/study/NCT03109652> 13 pages. Posting date: Jan. 8, 2019 (Year: 2019).

Office Action dated Dec. 29, 2025, U.S. Appl. No. 19/366,287, 18 pages.

"Peri-articular Tranexamic Acid Injection in Total Knee Arthroplasty" National Library of Medicine, NCT02829346 (2016), 13 pages.

Pinsornsak et al. (2021) "Efficacy and Systemic Absorption of Peri-articular Versus Intra-articular Administration of Tranexamic Acid in Total Knee Arthroplasty: A Prospective Randomized Controlled Trial" Arthroplasty Today, 1-5.

Sa-Ngasoongsong et al. (2011) "Postoperative blood loss reduction in computer-assisted surgery total knee replacement by low dose intra-articular tranexamic acid injection together with 2-hour clamp drain: a prospective triple-blinded randomized controlled trial" Orthopedic Reviews, 3:e12.

Examination Report dated Mar. 16, 2026, Appln. No. EP 25211111.7, 5 pages.

European search report dated Mar. 4, 2026, Appln. No. EP 25211111.7, 4 pages.

* cited by examiner

FIG. 1
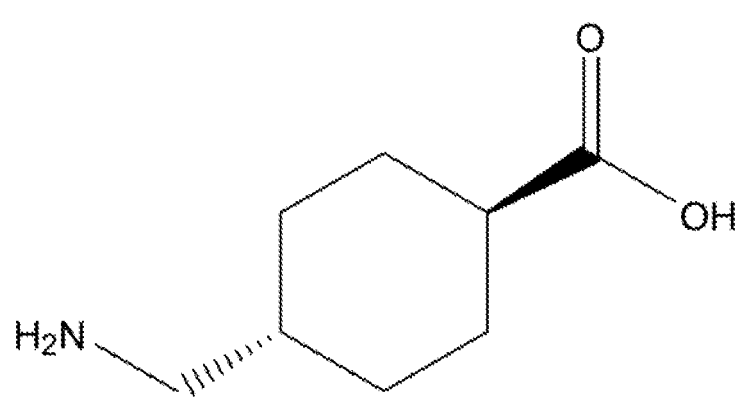
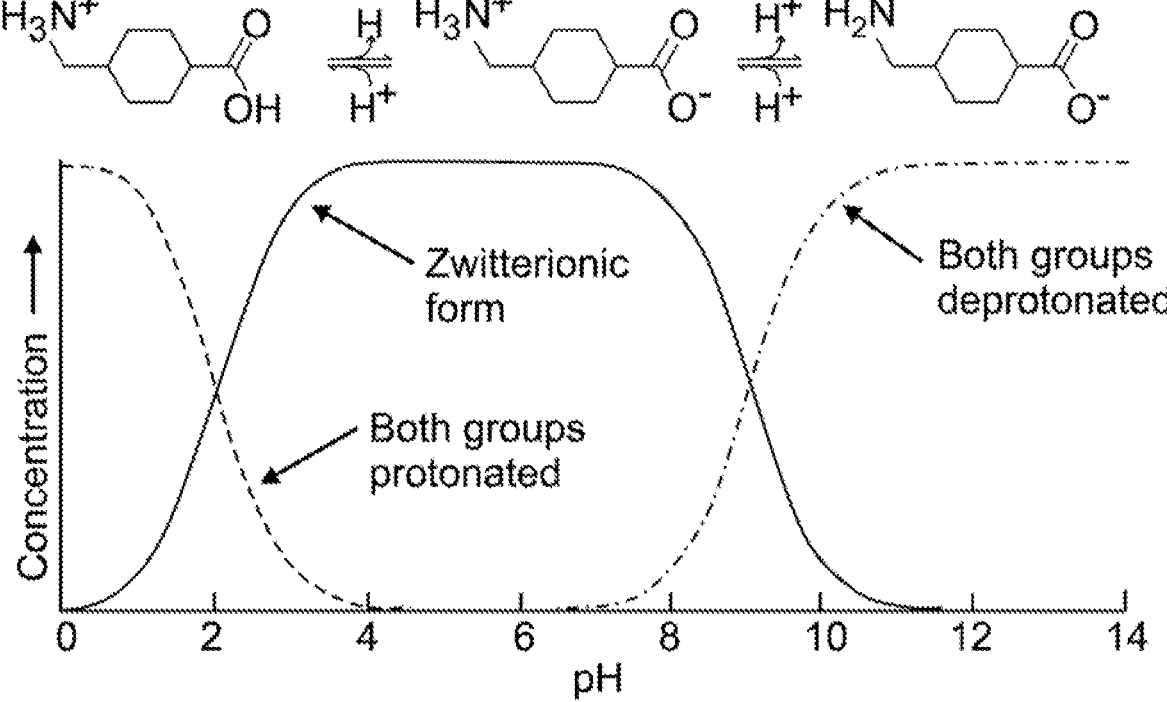
FIG. 2

300

310
320
330
340
350
360
370
380
390

305

340
345
370
375

490 400 440 420 410

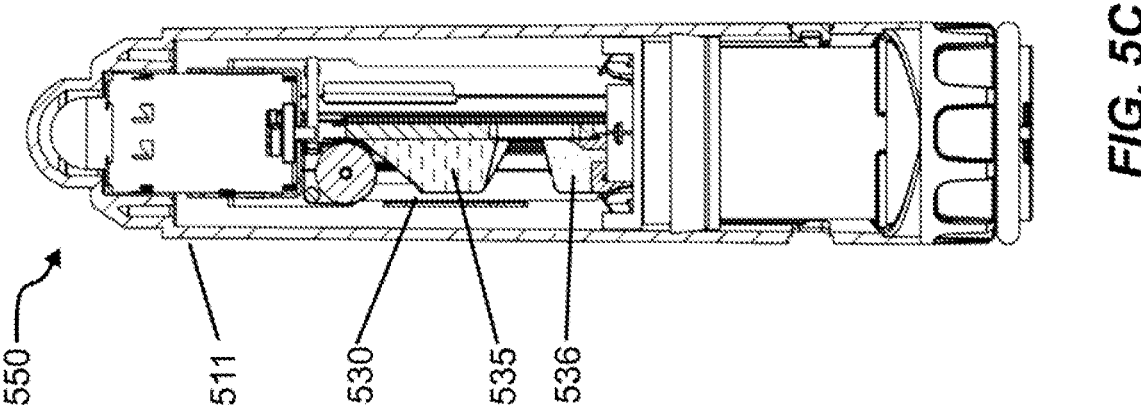
*FIG. 5C*
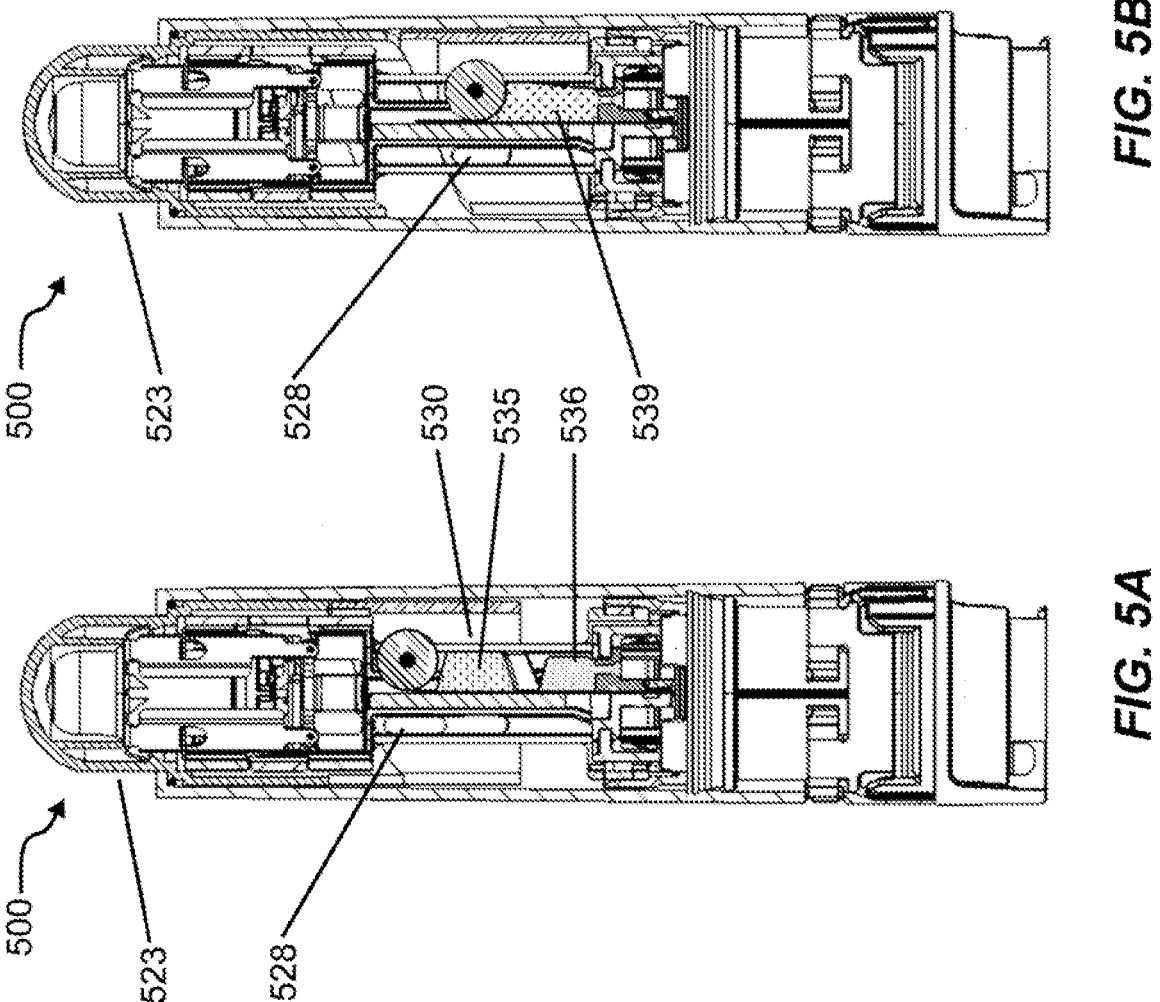
*FIG. 5B*
*FIG. 5A*

Group 2  dosing=1000, formulation=0 (IV) Dose in ug

—Predicted    · Observed

Group 3  dosing=1000, formulation=1 (IM) Dose in ug

—Predicted    · Observed

Group 4  dosing=2000, formulation=1 (IM) Dose in ug

—Predicted   ·Observed

CONCENTRATED INJECTABLE TRANEXAMIC ACID COMPOSITIONS AND METHODS OF USE THEREOF

CROSS-REFERENCES TO RELATED APPLICATIONS

This application claims the benefit of U.S. Provisional Application No. 63/308,367, filed Feb. 9, 2022, and U.S. Provisional Application No. 63/340,298, filed May 10, 2022, the disclosure of each of which is incorporated by reference herein in its entirety.

BACKGROUND

Hemorrhage is the leading cause of preventable death on the battlefield with very high mortality rates among the victims of non-compressible hemorrhage. Noncompressible hemorrhage cannot be controlled by direct pressure and requires evacuation to a surgical capable facility. Pre-hospital treatment options are extremely limited.

Tactical Combat Casualty Care (TCCC) guidelines call for tranexamic acid (TXA) as the first drug to be administered to casualties anticipated to need significant blood transfusion.

For maximum efficacy TXA must be administered immediately after injury, but current practices result in treatment delays and lost treatment opportunities.

Tranexamic acid (TXA) is an antifibrinolytic hemostatic used in severe hemorrhage. TXA is known to improve survival in traumatic hemorrhage as has been demonstrated by several clinical studies. For maximum efficacy, TXA must be administered immediately after injury, but current practices result in treatment delays and lost treatment opportunities. A typical TXA adult dose may be up to 1,000 mg or more. TXA is typically supplied in a glass vial at 100 mg/mL, diluted in saline and administered by intravenous (IV) infusion over 10 minutes, which is time-consuming and not always feasible on the battlefield. Intraosseous (10) administration of TXA is a potential alternative; however, TXA would still monopolize the dedicated IO line that would not be available for transfusion.

An optimal way of administering TXA in challenging battlefield conditions would be by intramuscular (IM) injection with an auto-injector. A TXA auto-injector would enable early and rapid administration of TXA to large numbers of casualties as well as self- and buddy-administration.

One problem with TXA IM injections can be volume limitation to no more than about 5 mL per injection, while the dosage of TXA may be up to 1,000 mg or more. TXA exhibits limited water solubility of 167 mg/mL. (Merck Index, 9390, 10$^{th}$ Ed., 1983; Kane et al., 2021, Eur J Pharmaceutical Sci 164, 105893). Concentrated compositions comprising tranexamic acid or a pharmaceutically acceptable salt thereof at 200 mg/mL or more suitable for IM injection are desirable.

SUMMARY

Concentrated tranexamic acid compositions suitable for intramuscular administration are provided. The concentrated tranexamic acid compositions enable the use of a syringe and an auto-injector to facilitate rapid, reliable, and simple self or buddy administration, under extreme duress on the battlefield, by minimally trained users.

Ready-to-use intramuscular pharmaceutical compositions are provided comprising tranexamic acid or a pharmaceutically acceptable salt thereof in solution at 200 mg/mL to 600 mg/mL, about 300 mg/mL to about 550 mg/mL, about 400 mg/mL to about 550 mg/mL, about 450 mg/mL to about 550 mg/mL, about 475 mg/mL to about 525 mg/mL, or about 400 mg/mL, about 425 mg/mL, about 450 mg/mL, about 475 mg/mL, about 500 mg/mL, about 525 mg/mL, about 550 mg/mL, about 575 mg/mL, or about 600 mg/mL, or any concentration in between.

A ready-to-use intramuscular pharmaceutical composition is provided comprising tranexamic acid or a pharmaceutically acceptable salt thereof, the composition having a pH of no more than about pH 5.0, no more than about pH 4.5, or no more than about pH 4.0, or having a pH within the range of from about pH 3.0 to about 5.0, from about pH 3.0 to about pH 4.5, or from about pH 3.0 to about pH 4.0.

The pharmaceutical composition of the disclosure may comprise at least about 200 mg/mL, or from 200 mg/mL to 600 mg/mL, about 300 mg/mL to about 550 mg/mL, about 400 mg/mL to about 550 mg/mL, about 450 mg/mL to about 550 mg/mL, about 475 mg/mL to about 525 mg/mL, or about 400 mg/mL, about 425 mg/mL, about 450 mg/mL, about 475 mg/mL, about 500 mg/mL, about 525 mg/mL, about 550 mg/mL, about 575 mg/mL, or about 600 mg/mL of the tranexamic acid or pharmaceutically acceptable salt thereof in solution. The pharmaceutical composition of the disclosure may be an aqueous solution that requires no dilution before administration. The aqueous solution may be a clear, homogenous aqueous solution.

The pharmaceutical composition according to the disclosure may comprise one or more additives selected from the group consisting of pH adjuster, tonicity agent, anesthetic, buffer, solvent, preservative, carrier, and colorant. The pharmaceutical composition may include a pH adjuster that is hydrochloric acid. The tonicity agent may be selected from the group consisting of sodium chloride, glycerin, mannitol, dextrose, and trehalose. The pharmaceutical composition may have a tonicity between about 270 to about 340 mOsm/kg, about 280 to about 320 mOsm/kg, or about 290 to about 310 mOsm/Kg. The solvent may be selected from the group consisting of ethyl alcohol, isopropyl alcohol, methanol, polyethylene glycol, propylene glycol, benzyl benzoate, dimethyl sulfoxide, dimethyl formamide, acetone, acetonitrile, butanone, and solketal. The carrier may be an albumin such as a human albumin, a recombinant human albumin, or a cyclodextrin. The cyclodextrin may be a beta-cyclodextrin, for example, a 2-hydroxypropyl-beta-cyclodextrin or a sulfobutylether-beta-cyclodextrin.

In some instances, the pharmaceutical composition does not include liposomes.

A pharmaceutical composition for parenteral administration is provided comprising a ready-to-use aqueous solution comprising from 300 to about 600 mg/mL tranexamic acid or a pharmaceutically acceptable salt thereof; and a pH adjuster in an amount to provide initial pH from about 3.0 to about 5.0. The pharmaceutical composition may comprise from about 450 to about 550 mg/mL tranexamic acid or a pharmaceutically acceptable salt thereof; and a pH adjuster in an amount to provide initial pH from about 3.5 to about 4.5.

The pharmaceutical composition may comprise a tonicity agent, optionally wherein the tonicity agent is about 0.9% (w/v) sodium chloride.

The pharmaceutical composition may include an anesthetic such as benzyl alcohol. In some embodiments, the pharmaceutical composition may comprise from about 2% to about 6%, about 3% to about 5%, or about 3.5% to about 4.5% (v/v) benzyl alcohol.

The pharmaceutical composition may require no dilution before administration.

The pharmaceutical composition according to the disclosure when stored for 6 months at 25° C. at 60% RH may be capable of maintaining: a pH within about ±0.5 points compared to starting pH at t=0; and a concentration of tranexamic acid within ±10% of the starting concentration at t=0. In some embodiments, the pharmaceutical composition according when stored for 6 months at 40° C. at 75% RH may be capable of maintaining a pH within about ±0.5 points compared to starting pH at t=0; and a concentration of tranexamic acid within ±10% of the starting concentration at t=0.

The disclosure provides a use of the pharmaceutical composition for manufacture of a medicament for treating hemorrhage in a subject in need thereof.

A method of treating or preventing hemorrhage in a subject in need thereof is provided, comprising parenterally administering an effective amount of the pharmaceutical composition according to the disclosure. The administration may be intramuscular administration. In some embodiments, the subject exhibits onset of a tranexamic acid plasma concentration of at least about 15 μg/mL within about 5 minutes, about 6 minutes, about 7 minutes, about 8 minutes, about 9 minutes, or within about 10 minutes, following intramuscular administration of the composition comprising at least about 1.0 g of the tranexamic acid or a pharmaceutically acceptable salt thereof. In some embodiments, the subject exhibits a tranexamic acid plasma concentration of at least about 15 μg/mL for at least about 100 min, at least about 110 min, or at least about 120 min following intramuscular administration of the composition comprising at least about 1.0 g of the tranexamic acid or a pharmaceutically acceptable salt thereof. In some embodiments, the subject exhibits a tranexamic acid plasma (max of no more than about 40 μg/mL, or no more than about 37 μg/mL, following intramuscular administration of the composition comprising about 1.0 g of the tranexamic acid or a pharmaceutically acceptable salt thereof.

An auto-injector arrangement is provided, comprising an auto-injector comprising an injector body housing the pharmaceutical composition according to the disclosure. The auto-injector arrangement may include an injector body comprising a first compartment comprising a first flexible primary container for storing the pharmaceutical composition, and optionally at least a second compartment comprising a second flexible primary container for storing the pharmaceutical composition or at least one additional active agent separate from the pharmaceutical composition. The auto-injector arrangement may include wherein the at least one additional active agent is selected from the group consisting of an anesthetic, analgesic, and antimicrobial agent.

An auto-injector arrangement is provided comprising an auto-injector comprising an injector body housing a ready-to-mix pharmaceutical composition comprising a therapeutically effective amount of tranexamic acid or a pharmaceutically acceptable salt thereof; and an aqueous diluent which when mixed with the ready-to-mix composition is capable of forming an injectable pharmaceutical composition. In some embodiments, the auto-injector arrangement comprises an injector body wherein the injector body comprises a first flexible primary container for storing the ready-to-mix pharmaceutical composition, a second flexible primary container for storing the aqueous diluent separate from the ready-to-mix pharmaceutical composition. In some embodiments, the auto-injector arrangement is capable of forming an injectable pharmaceutical composition having a pH of no more than pH 5.0, no more than pH 4.5, or no more than pH 4.0.

In some embodiments, the auto-injector arrangement comprises wherein the primary container is in communication with an intramuscular injection needle, the primary container having a volume capacity capable of housing at least 2 mL, at least 3 mL, at least 4 mL, or at least 5 mL dose of the diluted injectable pharmaceutical composition. The plurality of primary containers may each be in communication with a plurality of intramuscular injection needles for administering the diluted injectable pharmaceutical composition to form multiple depots in the muscle. The plurality of primary containers may accumulatively comprise a volume capacity capable of housing at least 2 mL, at least 3 mL, at least 4 mL, or at least 5 mL dose of the diluted injectable pharmaceutical composition. In some embodiments, the primary container is in fluid communication with at least one intramuscular injection needle for administering the dose of diluted injectable pharmaceutical composition to form the plurality of depots in the muscle.

A kit is provided comprising a prefilled aseptic primary container comprising the pharmaceutical composition according to the disclosure. A kit is provided comprising an auto-injector arrangement comprising a first flexible primary container comprising the pharmaceutical composition according to the disclosure, and optionally a sheet of instructions.

BRIEF DESCRIPTION OF THE DRAWINGS

FIG. 1 shows a representative chemical structure of tranexamic acid.

FIG. 2 shows a graph with representative pH-dependent solubility curves of amino acids (lower panel). The upper panel shows a scheme of a fully protonated form, a zwitterionic form, and a deprotonated form of TXA, left to right, respectively. The zwitterionic form of TXA predominates at pH values close to its isoelectric point (~pH 7.3). Zwitterions have relatively poorer solubility than fully protonated and deprotonated forms.

FIG. 5A shows a cross-section view of a reconstitution auto-injector in the pre-reconstitution state.

FIG. 5B shows a cross-section view of a reconstitution auto-injector in the reconstituted state.

FIG. 5C show a cross-section view of a variant reconstitution auto-injector in the pre-reconstitution state.

DETAILED DESCRIPTION OF THE INVENTION

Figures 3A, 3B, 4:
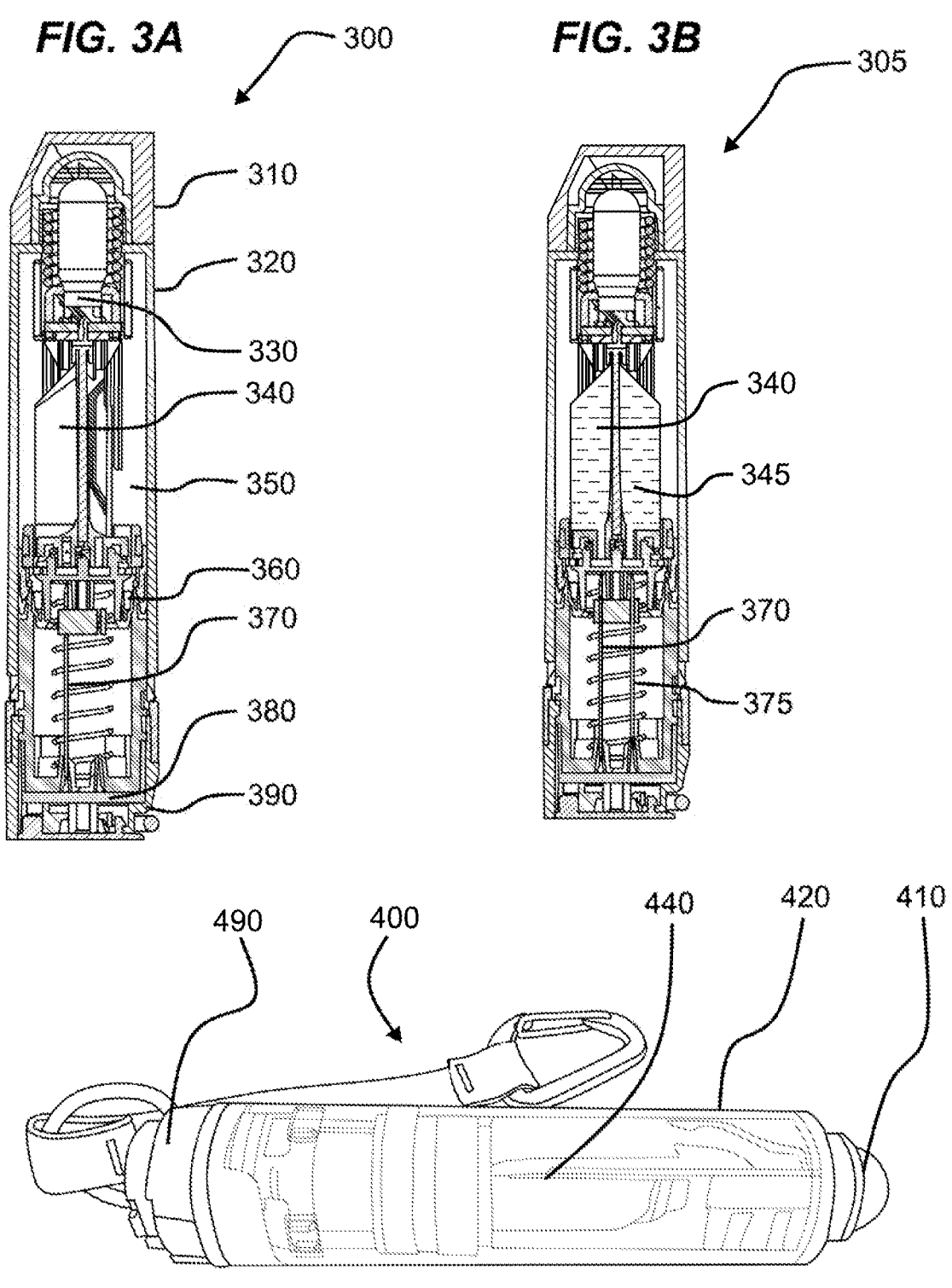
FIG. 3A shows an auto-injector arrangement 300 with a single chamber configuration schematic showing the major components of the device.
FIG. 3B shows an auto-injector arrangement 305 with a double chamber configuration schematic showing the major components of the device.
FIG. 4 shows an auto-injector arrangement 400 with a single chamber configuration schematic.

The majority of US combat fatalities between 2001 and 2011 occurred on the battlefield (87%) of which 24% were potentially survivable. Hemorrhage was the cause of death in 90.9% of the potentially survivable cases, underscoring the importance of early hemorrhage control.

Since 2001, battlefield trauma care has improved dramatically with the increased use of tourniquets, blood transfusions and blood products, shortening of hospital transport times (defined as the Golden Hour and the "Gates Effect"), and the introduction of tranexamic acid (TXA) collectively producing a 44% reduction in mortality between 2011 and 2017 in the Afghanistan and Iraq conflicts.

Non-compressible hemorrhage cannot be controlled by direct pressure and requires evacuation to a surgical capable facility. Pre-hospital treatment options are extremely limited and include resuscitative thoracotomy with aortic cross-clamping and endovascular aortic occlusion (e.g., resuscitative endovascular balloon occlusion of the aorta (RE-BOA)) but are not always feasible and can only be applied for limited periods of time—60 minutes is considered to be the maximum duration of complete occlusion before salvaging the patient is no longer possible.

TXA is well-known to improve survival in traumatic hemorrhage as has been demonstrated by dozens of clinical studies. Notably, The American College of Surgeons-Committee on Trauma, the American College of Emergency Physicians, and the National Association of EMS Physicians each specifically advise to administer TXA to patients with non-compressible bleeding.

Tranexamic acid (TXA), also known as trans-4-(aminomethyl) cyclohexanecarboxylic acid, CAS RN: 1197-18-8, is an antifibrinolytic hemostatic agent that may be used to prevent or treat severe hemorrhage. A representative chemical structure of tranexamic acid is shown in FIG. 1.

TXA is a synthetic analog of the amino acid lysine that acts as an antifibrinolytic by reversibly binding to lysine receptor sites on plasminogen and competing with fibrin for the lysine-binding sites. This prevents conversion of plasminogen into the fibrinolytic enzyme plasmin by fibrin-bound tissue plasminogen activator (tPA). As a result, TXA lowers plasmin levels, thereby preserving the framework of fibrin's matrix structure and maintaining clot strength. TXA is commonly used to treat or prevent excessive blood loss in a variety of situations, including major trauma, surgeries with high risk of blood loss, dental procedures in hemophiliacs, heavy menstrual bleeding, and other conditions with intense bleeding. TXA remains functional even in severe metabolic acidosis, which is especially important in trauma and field care. The Military Application of Tranexamic Acid in Trauma Emergency Resuscitation (MATTERs) Study clearly demonstrated the efficacy of TXA in improving survival of bleeding casualties, especially those requiring massive transfusion.

TXA can be injected intramuscularly (IM), enabling the use of an auto-injector to facilitate rapid, reliable, and simple self or buddy administration, under extreme duress on the battlefield, by minimally trained users.

A recent prospective, open-label study comparing pharmacokinetics (PK) of intravenous (IV) and IM administration of TXA in bleeding trauma patients Trauma INTACT (NCT03875937), was performed by London School of Hygiene and Tropical Medicine (LSHTM). The study showed a bioavailability of IM TXA of 77%. The 1 gram TXA IM dose was given as two 5 ml (0.5 g each) injections into the thigh, gluteal or deltoid muscle. The injections were well-tolerated and therapeutic plasma concentrations were reached within 15 minutes of injection.

Auto-injectors are known to provide a distinct advantage in IM administration in that drugs administered via auto-injector are typically absorbed at a faster rate than the regular needle and syringe method, and PK parameters may more closely resemble those of IV administration.

This may be the result of the force of injection, which leads to broader dispersion of the administered drug, followed by faster absorption and distribution. Examples of this type of effect include studies with the EpiPen, the AtroPen, and the Astra Tech auto-injectors which show faster absorption and earlier onset of action compared to the needle and syringe administration.

A concentrated solution comprising tranexamic acid or a pharmaceutically acceptable salt thereof for intramuscular injection is desirable. A method of treating severe hemorrhage in a subject in need thereof is desirable. Compositions and methods to prevent, alleviate, or decrease the extent of hemorrhage in a subject, for example, in response to an emergency event such as a traumatic injury, childbirth, or surgical procedure are also desirable.

Definitions

The singular forms "a", "an" and "the" are intended to include the plural forms as well, unless the context clearly indicates otherwise.

The term "and/or" refers to and encompasses any and all possible combinations of one or more of the associated listed items.

The term "about," as used herein when referring to a measurable value such as an amount of a compound, dose, time, temperature, and the like, is meant to encompass variations of 10%, 5%, 1%, 0.5%, or 0.1% of the specified amount.

Unless otherwise specified, all percentage "%" values are expressed as weight percent compared to total weight of the composition.

The terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this disclosure belongs. In the event of conflicting terminology, the present specification is controlling.

The term "therapeutically effective amount" refers to the amount of a compound that, when administered to a subject for treating an injury, disease or condition, is sufficient to effect such treatment to fully, substantially, or partially alleviate the symptoms of the disease state or condition. The "therapeutically effective amount" can vary depending on the injury and its severity, and the condition, age, weight, gender etc. of the subject to be treated. In some embodiments, the effective amount of tranexamic acid is the amount sufficient to prevent or measurably alleviate duration and/or severity of hemorrhage during and following an emergency event such as a traumatic injury. For example, the ready to use pharmaceutical compositions provided herein may be used in trauma patients with significant hemorrhage. In some embodiments, the therapeutically effective amount of tranexamic acid or a pharmaceutically acceptable salt thereof is in a range of from about 0.5 g to about 2.5 g, or about 0.75 g to about 2.0 g, or about 0.75 g to about 1.5 g, or about 0.9 g to about 1.1 g, or about 0.5 g, about 0.6 g, about 0.7 g, about 0.8 g, about 0.9 g, about 1.0 g, about 1.1 g, about 1.2 g, about 1.3 g, about 1.4 g. about 1.5 g, about 1.6 g, about 1.7 g, about 1.8 g, about 2.0 g, about 2.1 g, about 2.2 g, about 2.3 g per dose, about 2.4 g, or about 2.5 g per dose.

The terms "treating" and "treatment" of a disease state or condition include: (i) preventing the disease state or condition, i.e., causing the clinical symptoms of the disease state or condition not to develop in a subject that may be exposed to or predisposed to the disease state or condition, but does not yet experience or display symptoms of the disease state or condition, (ii) inhibiting the disease state or condition, i.e., arresting the development of the disease state or condition or its clinical symptoms, or (iii) relieving the disease state or condition, i.e., causing temporary or permanent regression of the disease state or condition or its clinical symptoms. In some embodiments, the terms "treating" or "treatment" refer to prevention or alleviation of hemorrhage, for example, during and following an emergency event such as a traumatic injury, child birth, or surgical procedure.

The terms, "patient", "subject" or "subjects" include but are not limited to humans, the term may also encompass other mammals, such as service animals, domestic animals, or exotic animals, for example, dogs, cats, ferrets, rabbits, pigs, horses, cattle, birds, or reptiles.

The term "pharmaceutically acceptable" refers to compatibility with the other ingredients of the formulation and not deleterious to the recipient thereof.

The term "pharmaceutically acceptable salt" refers to salt forms of the active compounds which are prepared with counter ions which are non-toxic under the conditions of use and are compatible with a stable formulation. Non-limiting examples of pharmaceutically acceptable salts may include hydrochloride, sodium, sulfate, acetate, phosphate/diphosphate, chloride, potassium, maleate, calcium, citrate, mesylate, nitrate, tartrate, aluminum, and gluconate salts of the active ingredient.

The term "tranexamic acid or a pharmaceutically acceptable salt thereof" when in a dried form is intended to include anhydrous forms or hydrates thereof.

The term "room temperature" refers to controlled room temperature as between 20° C. to 25° C.

The term "solution" refers to a clear, homogeneous liquid dosage form that contains at least one active pharmaceutical chemical substance dissolved in a solvent or mixture of mutually miscible solvents.

The term "tonicity agent" refers to an agent added to an injectable composition to prevent osmotic shock at the site of injection upon administration, and which may reduce local irritation. The tonicity of a solution is related to its effect on the volume of a cell. Solutions that do not change the volume of a cell are isotonic.

The term "osmolality" refers to the concentration of a solution in terms of osmoles of solutes, per kilogram of solvent. Typically, a solution having an osmolality of about 280 to about 320 mOsm/kg is considered isotonic. If a cell is placed in a hypertonic solution, water will leave the cell, and the cell will shrink. If a cell is placed in a hypotonic solution, the cell will take up water from the solution, causing the cell to swell.

The term "Cmax" refers to the maximum observed drug plasma concentration.

The term "AUCINF_pred" refers to the area under the curve of the drug plasma concentration over time from t=0 to infinity predicted.

The term "Tmax" refers to the time point corresponding to the maximum concentration of the drug in plasma after administration.

The acronym "AUC" refers to The area under the curve, from t=0 to t=T (last measurable plasma concentration), and from t=0 to infinity (by extrapolation).

The term "HL_Lambda_z" refers to terminal half-life.

The term "terminal half-life" or "plasma terminal half-life" refers to the time required to divide the plasma concentration of a drug by two after reaching pseudo-equilibrium.

All patents, patent applications and publications referred to herein are incorporated by reference in their entirety.

The embodiments described in one aspect of the present disclosure are not limited to the aspect described. The embodiments may also be applied to a different aspect of the disclosure as long as the embodiments do not prevent these aspects of the disclosure from operating for its intended purpose.

Compositions

Pharmaceutical compositions comprising tranexamic acid or a pharmaceutically acceptable salt thereof are provided herein. The pharmaceutical compositions of the disclosure may be used for intramuscular injection. Ready-to-use, pharmaceutical compositions comprising tranexamic acid and water for injection are provided herein which are suitable for intramuscular administration. The ready-to-use pharmaceutical compositions described herein comprise tranexamic acid or a pharmaceutically acceptable salt thereof as the active ingredient, water, and a pH adjuster. Optionally, the pharmaceutical compositions may include a tonicity agent.

In some embodiments, the pharmaceutical composition of the disclosure does not include an antibiotic agent. In some embodiments, the pharmaceutical composition of the disclosure does not include liposomes.

The term "ready-to-use" or "ready to use" refers to a pre-mixed pharmaceutical composition that does not require reconstitution or dilution before administration to a subject.

The ready-to-use pharmaceutical compositions provided herein are stable when stored at room temperature for 6 months or longer. In some embodiments, suitable buffers and/or co-solvents may be added to the pharmaceutical compositions. Co-solvents may include an ethanol, propylene glycol, polyethylene glycol, or the like. In some embodiments, no buffer and/or no co-solvent is employed.

Ready-to-use pharmaceutical compositions are provided comprising 200 to 600 mg/mL, 300 to 550 mg/mL, or about 500 mg/mL tranexamic acid or a pharmaceutically acceptable salt thereof, pH 3.0-5.0, that when stored for 6 months at room temperature conditions of about 25° C. at about 60% RH are capable of maintaining: a pH within about ±0.5 points compared to starting pH at t=0; and a concentration of tranexamic acid within ±10%, ±5%, or +4% of the starting concentration of the tranexamic acid or a pharmaceutically acceptable salt thereof at t=0.

Ready-to-use pharmaceutical compositions are provided comprising 200 to 600 mg/mL, 300 to 550 mg/mL, or about 500 mg/mL tranexamic acid or a pharmaceutically acceptable salt thereof, pH 3.0-5.0, that when stored for 6 months under accelerated conditions of about 40° C. at about 75% RH are capable of maintaining: a pH within about ±0.5 points compared to starting pH at t=0; and a concentration of tranexamic acid within ±10%, ±5%, or ±4% of the starting concentration of the tranexamic acid or a pharmaceutically acceptable salt thereof at t=0.

The disclosure provides aqueous pharmaceutical compositions comprising tranexamic acid or a pharmaceutically acceptable salt thereof, the composition having a pH of no more than about pH 5.0, a pH in a range of from about pH 3.0 to about 5.0, from pH 3.0 to 4.5, from pH 3.5 to 4.5, or about pH 3. S, about pH 4.0, about pH 4.5, or about pH 5.0. The pharmaceutical compositions of the disclosure may be suitable for intramuscular injection.

The pharmaceutical compositions of the disclosure may comprise one or more pH adjusters. The pH adjuster may be any pharmaceutically acceptable pH adjuster known in the art. In some embodiments, the pH adjuster is selected from hydrochloric acid, nitric acid, sulfuric acid, hydrobromic acid, citric acid, malic acid, adipic acid, ascorbic acid, tartaric acid, lactic acid, phosphoric acid, and combinations thereof. In some embodiments, the pH adjuster is hydrochloric acid. The pH adjuster may be employed in the composition in an amount to adjust the pH range as specified. For example, the pH adjuster may in the range of about 0.1 wt % to 1 wt %, or about 0.2 to 0.5 wt %, or about 0.3 to 0.4 wt %.

The pharmaceutical compositions of the disclosure may comprise one or more injectable local anesthetics. The injectable local anesthetic may be any appropriate injectable local anesthetic known in the art. The injectable local anesthetic may be, for example, one or more of benzyl alcohol, lidocaine, mepivacaine, articaine, prilocaine, tetracaine, procaine, chloroprocaine, bupivacaine, and dibucaine.

The pharmaceutical composition may include from 0 to 6% 0.5 to 5%, 2 to 5%, or 0.5%, 1.0%, 1.5%, 2.0%, 2.5%, 3.0%, 3.5%, 4.0%, 4.5%, 5.0%, 5.5%, or 6.0%, or any value in between, of the injectable local anesthetic.

The injectable local anesthetic may be benzyl alcohol. Intradermal injections of 1 ml 0.9% benzyl alcohol with epinephrine have been reported to provide prolonged cutaneous anesthesia, although it is not as effective as lidocaine with epinephrine. However, benzyl alcohol is significantly less painful on injection than lidocaine with epinephrine. (see, e.g., Wilson and Martin, Benzyl alcohol as alternative local anesthetic, Ann Emerg Med 1999 May; 33 (5): 495-499). The pharmaceutical composition may include from 0 to 6%, 0.5 to 5%, 2 to 5%, about 1%, about 2%, about 3%, about 3.5%, about 4%, about 4.5%, about 5.0%, about 5.5%, about 6% (v/v) benzyl alcohol.

The pharmaceutical compositions of the disclosure may comprise one or more tonicity agents. Typically, tonicity agents are used to adjust the osmolality of the ready-to-use pharmaceutical compositions to bring it closer to the osmotic pressure of body fluids, such as blood or plasma. In some embodiments, the tonicity of the ready-to-use formulation can be modified by adjusting the concentration of other components present in the ready-to-use formulation. Provided that the compositions are physiologically compatible, the compositions do not require any particular osmolality. Thus, the compositions can be hypotonic, isotonic or hypertonic. In some preferred embodiments, the compositions are isotonic with blood with range of 270-340 mOsmol/Kg. Typically, the ready-to-use pharmaceutical compositions may have a tonicity between about 270 to about 340 mOsm/Kg, about 280 to about 330 mOsm/Kg, or about 290 to about 310 mOsm/Kg.

Suitable tonicity agents for use in the ready-to-use pharmaceutical compositions include, but are not limited to, anhydrous or hydrous forms of sodium chloride, dextrose, sucrose, xylitol, fructose, glycerol, sorbitol, mannitol, trehalose, potassium chloride, mannose, calcium chloride, magnesium chloride, and other inorganic salts.

The quantity of the tonicity agent in the formulation can be expressed in mg/ml or in g/L. In typical embodiments, the optional tonicity agent(s) may be present from about 0 mg/ml to about 15 mg/ml, at about 5 mg/mL to about 10 mg/ml, or about 9 mg/ml.

The tonicity agent may be sodium chloride. The ready-to-use pharmaceutical composition may comprise sodium chloride in a concentration of from about 0 to about 1% wt/vol, from about 0.5 to about 1.0%, or about 0.90% wt/vol. The ready-to-use pharmaceutical composition may comprise sodium chloride in a concentration of from about 5 mg/mL to about 10 mg/mL, or about 9.0 mg/mL. In some embodiments, the amount of sodium chloride in the formulations is determined based on experimentally established osmolality of the tranexamic acid or pharmaceutically acceptable salt thereof in water for injection in a range of from 300 mg/mL to 600 mg/mL, 400 mg/mL to 600 mg/mL, 450 mg/mL to 550 mg/mL, or about 500 mg/mL, respectively. In some embodiments, no tonicity agent is employed.

The pharmaceutical compositions of the disclosure may comprise a buffer. In some embodiments, no buffer is employed.

A buffer solution is an aqueous solution comprising a mixture of a weak acid and its conjugate base, or a weak base and its conjugate acid. Buffer solutions may be used as a means of keeping pH at a near constant value. Any suitable buffers known in the art may be employed in the pharmaceutical compositions described herein. Buffers may include, but are not limited to, pharmaceutically acceptable salts and acids of acetic acid/sodium acetate, citric acid/sodium citrate, citric acid/sodium phosphate dibasic, citric acid/sodium hydroxide, succinate, tartrate, benzoate, lactate, histidine or other amino acids, gluconate, phosphate, malate, formate, propionate, phosphate, phosphate buffered saline, acetate, glutamate, magnesium, and carbonate.

The concentration of the buffer in the formulation can be expressed in mg/ml, g/L or as a molar concentration. Optionally, the composition may comprise from about 0.0001 mg/ml to about 100 mg/ml of a suitable buffer is present in the pharmaceutical compositions. Thus, the ready-to-use pharmaceutical compositions can comprise from about 0.0001 to about 0.001 mg/ml of a suitable buffer, from about 0.001 to about 0.01 mg/ml of a suitable buffer, from about 0.01 to about 0.1 mg/ml of a suitable buffer, from about 0.1 to 1 mg/ml of a suitable buffer, from about 1 to about 5 mg/ml of a suitable buffer, from about 5 to about 10 mg/ml of a suitable buffer, from about 10 to about 15 mg/ml of a suitable buffer, from about 15 to about 20 mg/ml of a suitable buffer, from about 20 to about 25 mg/ml of a suitable buffer, from about 25 to about 50 mg/ml of a suitable buffer, from about 50 to about 75 mg/ml of a suitable buffer, and from about 75 to about 100 mg/ml of a suitable buffer.

Alternatively, the buffer concentration can be expressed as molar concentrations. In typical embodiments, from about 0.1 to 100 mM of a suitable buffer is present in the pharmaceutical compositions. Thus, the ready-to-use pharmaceutical compositions can optionally comprise a suitable buffer having a concentration from about 0.1 to about 100 mM, from about 0.1 to about 0.5 mM, from about 0.5 to about 1.0 mM, from about 1.0 to about 5 mM, from about 5 to about 10 mM, from about 10 to about 15 mM, from about 15 to about 25 mM, from about 25 to about 50 mM, from about 50 to about 75 mM, and from about 75 to about 100 mM.

A ready-to-use pharmaceutical composition comprising tranexamic acid or a pharmaceutically acceptable salt thereof is provided in about 500 mg/ml concentration in water for injection comprising a tonicity agent and a pH adjuster at a pH in a range of pH 3.0 to 5.0 in a 1 ml volume. This will provide a 500 mg dose of tranexamic acid.

A ready-to-use pharmaceutical composition comprising tranexamic acid or a pharmaceutically acceptable salt thereof is provided in about 500 mg/ml concentration in water for injection comprising a tonicity agent and a pH adjuster at a pH in a range of pH 3.0 to 5.0 in a 2 ml volume. This will provide a 1,000 mg dose of tranexamic acid.

A ready-to-use pharmaceutical composition comprising tranexamic acid or a pharmaceutically acceptable salt thereof is provided in about 500 mg/ml concentration in water for injection comprising a tonicity agent and a pH adjuster at a pH in a range of pH 3.0 to 5.0 in a 4 ml volume. This will provide a 2,000 mg dose of tranexamic acid.

A ready-to-use pharmaceutical composition comprising tranexamic acid or a pharmaceutically acceptable salt thereof is provided in about 500 mg/ml concentration in water for injection comprising benzyl alcohol and a pH adjuster at a pH in a range of pH 3.0 to 5.0 in a 1 ml volume. This will provide a 500 mg dose of tranexamic acid.

A ready-to-use pharmaceutical composition comprising tranexamic acid or a pharmaceutically acceptable salt thereof is provided in about 500 mg/ml concentration in water for injection comprising benzyl alcohol and a pH adjuster at a pH in a range of pH 3.0 to 5.0 in a about 2 ml volume. This will provide a 1,000 mg dose of tranexamic acid.

A ready-to-use pharmaceutical composition comprising tranexamic acid or a pharmaceutically acceptable salt thereof is provided in about 500 mg/ml concentration in water for injection comprising benzyl alcohol and a pH adjuster at a pH in a range of pH 3.0 to 5.0 in a 4 ml volume. This will provide a 2,000 mg dose of tranexamic acid.

In some embodiments, the pharmaceutical compositions of the disclosure may be employed with an additional active agent separate from the pharmaceutical composition. For example, an additional active agent separate from the pharmaceutical composition of the disclosure may be provided in an auto-injector arrangement.

The additional active agent may be, for example, an anesthetic, analgesic, epinephrine, or antibiotic. The additional active agent may be an analgesic such as an injectable opioid agonist. The injectable opioid agonist may be, for example, morphine, meperidine, fentanyl, or hydromorphone. Other injectable analgesics may be, for example, ketolorac, ibuprofen, paracetamol, ketamine, and magnesium sulfate. (Abdolrazaghnejad et al., 2018, Adv J Emergency Medicine, 2(4):e45).

The additional active agent may be any appropriate injectable anesthetic. The injectable anesthetic may be, for example, one or more of benzyl alcohol, procaine, chloroprocaine, lidocaine, prilocaine, tetracaine, bupivacaine, and dibucaine.

The additional active agent may be epinephrine. Among adult patients with traumatic cardiac arrest (TCA), administration of epinephrine in the prehospital setting was associated with increased short-term survival, especially for those with a longer prehospital time. (Chiang et al. Scandinavian Journal of Trauma, Resuscitation and Emergency Medicine (2015) 23:102 DOI 10.1186/s13049-015-0181-4).

The additional active agent may be any appropriate antimicrobial agent. The antimicrobial agent may be, for example, cefazolin, cephalexin, cefotaxime, ceftazidime, erythromycin, clindamycin, fluoroquinolone, levofloxacin, cephalosporin, ceftriaxone, metronidazole, or bacitracin.

Administration

The pharmaceutical compositions according to the disclosure comprise tranexamic acid or a pharmaceutically acceptable salt thereof in aqueous solution and are intended to be suitable for intramuscular injection. The pharmaceutical compositions may be ready to use compositions.

Typically up to 5 mL has been cited for adults as the maximum volume for a single intramuscular injection. The maximum volume for intramuscular injection may be injection site dependent. Intramuscular injections may be limited in volume to no more than 2.5 to 5 mL per injection depending on injection site. When using an auto-injector, injection volume may be limited to no more than 5 mL due to technological practices rather than any technological limitations.

The intramuscular injection may be a single bolus injection, multiple bolus injection, or intermittent injection as needed, or from one, two, three, four or more consecutive times from the beginning of treatment.

The pharmaceutical compositions according to the disclosure may be suitable for intramuscular injection volumes of about 0.5 mL to about 5.0 mL, about 0.5 mL to about 4.0 mL, about 1.0 mL to about 3.0 mL, about 0.5 mL, about 0.75 mL, about 1.0 mL, about 1.5 mL, about 2.0 mL, about 2.5 mL, about 3.0 mL, about 3.5 mL, about 4.0 mL, about 4.5 mL, about 5.0 mL, or any volume in between.

The intramuscular injection site may be any suitable injection site. For example, the pharmaceutical compositions of the disclosure may be administered by intramuscular injection at an intramuscular injection site selected from deltoid, dorsogluteal, ventrogluteal, rectus femoris, and vastus lateralis.

The pharmaceutical compositions according to the disclosure may include a dosage of about 500 mg to about 2000 mg, about 550 mg to about 1500 mg, about 650 mg to about 1300 mg, about 800 mg to about 1200 mg, or about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg, or any amount in between of tranexamic acid or a pharmaceutically acceptable salt thereof per intramuscular injection.

The pharmaceutical compositions according to the disclosure may include a dosage of about 5 mg/kg to about 30 mg/kg, about 6 mg/kg to about 25 mg/kg, about 7 mg/kg to about 20 mg/kg, about 8 mg/kg to about 15 mg/kg, about 9 mg/kg to about 12 mg/kg, or about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about mg/kg, about 21 mg/kg, about 22 mg/kg, about 23 mg/kg, about 24 mg/kg, about 25 mg/kg, about 26 mg/kg, about 27 mg/kg, about 28 mg/kg, about 29 mg/kg, or about 30 mg/kg, or any amount in between of tranexamic acid or a pharmaceutically acceptable salt thereof per intramuscular injection.

Analytical Procedures pH Testing

The pharmaceutical compositions according to the disclosure may pass the pH test under USP<791> with variation ±0.5 pH unit compared to original pH when stored in a glass vial or flexible plastic container at room temperature at 25° C. at 60% relative humidity or 40° C. at 75% RH, for at least 6 months, 12 months, 18 months or more.

The pharmaceutical compositions according to the disclosure may have pH 3.0-5.0 by USP <791>, at manufacture and when stored at room temperature, or 25° C. at 60% relative humidity for at least 3 months, 6 months, 12 months, 18 months or more.

Active Pharmaceutical Ingredient and Impurities Testing

The pharmaceutical compositions according to the disclosure may exhibit tranexamic acid by HPLC of 95.0-105.0% of initial value under USP<621> when stored at room temperature for at least 3 months, 6 months, 12 months, 18 months or more.

In some embodiments, the pharmaceutical compositions according to the disclosure may exhibit not more than 0.1% tranexamic acid related impurity A by HPLC under USP<621> when stored at room temperature for at least 3 months, 6 months, 12 months, 18 months or more.

In some embodiments, the pharmaceutical compositions according to the disclosure may exhibit not more than 0.2% tranexamic acid related impurity B by HPLC under USP<621> when stored at room temperature for at least 3 months, 6 months, 12 months, 18 months or more.

In some embodiments, the pharmaceutical compositions according to the disclosure may exhibit not more than 0.1% tranexamic acid related impurity C by HPLC under USP<621> when stored at room temperature for at least 3 months, 6 months, 12 months, 18 months or more.

In some embodiments, the pharmaceutical compositions according to the disclosure may exhibit not more than 0.1% tranexamic acid related impurity D by HPLC under USP<621> when stored at room temperature for at least 3 months, 6 months, 12 months, 18 months or more.

In some embodiments, the pharmaceutical compositions according to the disclosure may exhibit not more than 0.05%, or 0.1%, of any single unspecified impurity by HPLC under USP<621> when stored at room temperature for at least 3 months, 6 months, 12 months, 18 months or more.

In some embodiments, the pharmaceutical compositions according to the disclosure may exhibit not more than 0.2% total unspecified impurities by HPLC under USP<621> when stored at room temperature for at least 3 months, 6 months, 12 months, 18 months or more.

The term "tranexamic acid related compound A" or "impurity A" refers to trans, trans-4,4'-iminodimethylenedi (cyclohexanecarboxylic acid), also known as tranexamic acid dimer, having CAS RN 93940-19-3. The term "tranexamic acid related compound B" or "impurity B" refers to cis-4-(aminomethyl)cyclohexanecarboxylic acid, also known as cis-tranexamic acid, having CAS RN: 1197-17-7. The term "tranexamic acid related compound C" or "impurity C" refers to (RS)-4-(aminomethyl)cyclohex-1-enecarboxylic acid, also known as 1,2-didehydro tranexamic acid, having CAS RN; 330838-52-3. The term "tranexamic acid related compound D" or "impurity D" refers to 4-(aminomethyl)benzoic acid, also known as benzylamine-4-carboxylic acid, having CAS RN: 56-91-7.

Particle Testing

The pharmaceutical compositions according to the disclosure may pass the Particulate matter test under USP<788> when stored at room temperature for at least 6 months, 12 months, 18 months or more. The pharmaceutical compositions according to the disclosure may pass the Visible Particles test under USP<790>, exhibiting absence of visible particles when stored at room temperature for at least 6 months, 12 months, 18 months or more.

The pharmaceutical compositions according to the disclosure may pass the Completeness of Solution Test under USP<641>, exhibiting a clear solution when stored at room temperature for at least 6 months, 12 months, 18 months or more. The pharmaceutical compositions according to the disclosure may pass the Color of Solution or Degree of Coloration test under Ph Eur 2.2.2, exhibiting colorless solution when stored at room temperature for at least 3 months, 6 months, 12 months, 18 months or more.

Microbial Testing

The pharmaceutical compositions according to the disclosure may exhibit ≤35 IU/ml Endotoxins by USP85>, at manufacture and when stored at room temperature for at least 3 months, 6 months, 12 months, 18 months or more.

The pharmaceutical compositions according to the disclosure may be sterile by USP <71>, at manufacture and when stored at room temperature for at least 3 months, 6 months, 12 months, 18 months or more.

Formulation Development for Intramuscular Injection

The technical barrier to a TXA auto-injector product is the low solubility of TXA compounded by the dose volume limitations of IM injections and of current auto-injector designs. One objective is to increase TXA solubility in order to develop the first TXA auto-injector. The proposed auto-injector arrangement can deliver up to a 5 ml dose.

Currently marketed parenteral TXA products are formulated in water for injection (WFI) at the concentration of 100 mg/mL (e.g., Cyklokapron, pH 6.5-8.0) or in sodium chloride at 10 mg/mL. In order to administer 1 g of TXA under the generally accepted maximum safe volume for IM injections (5 mL), the TXA would need to be formulated at concentrations higher than 200 mg/mL. Since the solubility of TXA in water is limited to 167 mg/mL, solubility enhancement was necessary.

The pKa of tranexamic acid is 4.3 and 10.6. The present inventors found that solubility of TXA could be increased by adjusting pH of the solution away from TXA's isoelectric point, where its solubility is lowest. The zwitterionic form of TXA predominates at pH values close to the isoelectric point (~pH 7.3). Zwitterions may have poorer solubility than fully protonated and deprotonated forms.

Several preliminary tests were performed using several different aqueous systems to confirm that TXA concentrations above 250 mg/mL are possible. A target concentration of 500 mg/mL would result in a total volume of 2 mL for 1 g of TXA, well under the 5 mL IM injection volume limit. The present inventors were able to achieve this concentration in normal saline (0.9% NaCl) using hydrochloric acid to lower the pH to 3.2.

The present inventors have developed TXA formulations at concentrations up to 500 mg/mL or more as described herein which allow delivering an effective intramuscular dose via auto-injector. Several potential flexible primary drug container materials were tested.

A pharmaceutical composition is provided comprising 200 mg/mL to 600 mg/mL tranexamic acid or a pharmaceutically acceptable salt thereof, 0.5-1.5% sodium chloride, 4N HCl, and water for injection, pH 3-5.

A pharmaceutical composition is provided comprising 400 mg/ml to 550 mg/mL tranexamic acid or a pharmaceutically acceptable salt thereof, 0.5-1.2% sodium chloride, 4N HCl, and water for injection, pH 3-5.

A pharmaceutical composition is provided comprising about 500 mg/mL tranexamic acid or a pharmaceutically acceptable salt thereof, 0.9% sodium chloride, 4N HCl, and water for injection, pH 3-4.

A pharmaceutical composition is provided comprising 200 mg/mL to 600 mg/mL tranexamic acid or a pharmaceutically acceptable salt thereof, 0.5-5% (v/v) benzyl alcohol, 4N HCl, and water for injection, pH 3-5.

A pharmaceutical composition is provided comprising 400 mg/mL to 550 mg/mL tranexamic acid or a pharmaceutically acceptable salt thereof, 3-5% (v/v) benzyl alcohol, 4N HCl, and water for injection, pH 3-5.

A pharmaceutical composition is provided comprising about 500 mg/mL tranexamic acid or a pharmaceutically acceptable salt thereof, 4% (v/v) benzyl alcohol, 4N HCl, and water for injection, pH 3-4.

Stability Studies

Stability studies of the new TXA formulation in flexible primary drug containers and standard glass vials were performed.

In order to design stability studies, compendial HPLC method (USP41: Tranexamic acid injection) per SOP-2004 Evaluation and Verification of Analytical Methods (USP <1226> Verification of Compendial Methods) was evaluated to ensure methods meet system suitability requirements for the intended use of determining stability of TXA. The method evaluation included: 1 week forced degradation storage, establishing specific method parameters, assessing sample prep requirements, and drafting the analytical methods. Method testing included demonstration of method precision, intermediate precision, accuracy, linearity/range, and specificity.

A stability study is ongoing and the most recent 15-month timepoint shows almost complete drug recovery and little change in pH at room temperature (25° C.±2° C./60%±5% RH) and in accelerated storage conditions (40° C.±2° C./75%±5% RH). Stability testing is being performed by using HPLC and pH assays. Considering that TXA is considered to be a stable molecule and that the flexible packaging materials provide moisture and oxygen barrier on par with glass in addition to being inert, the pharmaceutical compositions are considered to exhibit excellent shelf-life.

The pharmaceutical compositions provided herein may be capable of maintaining at least about 90%, 95%, 97.5%, 98%, 99%, 99.5%, or 99.7% of the release, or "as manufactured," amount of tranexamic acid in undegraded form after storage for at least 6 months, at least 12 months, or at least 18 months at 25° C. at 60% relative humidity when measured by liquid chromatography, e.g., high-pressure liquid chromatography (HPLC) by USP <621>.

The pharmaceutical compositions provided herein may be capable of maintaining at least about 90%, 95%, 97.5%, 98%, 99%, 99.5%, or 99.7% of the release, or "as manufactured," amount of tranexamic acid in undegraded form after storage for at least 6 months, at least 12 months, or at least 18 months at 40° C. at 75% relative humidity when measured by liquid chromatography, e.g., HPLC by USP <621>.

Pharmacokinetic Studies

The present inventors designed a study to compare the pharmacokinetic (PK) and pharmacodynamic (PD) profiles of TXA administration by IV, IM, and IM with auto-injector and assess toxicity in a GLP study in swine. The IND-enabling study was designed to provide the basis for advancing the IM-compatible formulation of TXA and a TXA auto-injector into clinical development.

The TXA formulation of the disclosure was administered by an intramuscular (IM) route of administration (TXA 500 mg/mL, pH 3-4), and compared against the commercially available formulation administered by an intravenous (IV) route of administration (TRANEX injection, TXA 100 mg/mL, pH 6.5-8.0), in female adult swine. The control item was vehicle –0.9% sodium chloride solution (pH 3-4, adjusted with HCl).

In some embodiments, the pharmaceutical composition of the disclosure (tranexamic acid, 500 mg/mL, pH 3-4) after IM administration of about 1 gram tranexamic acid to a subject, exhibits an Cmax in a range of from about 20 to about 35 ug/mL.

In some embodiments, the pharmaceutical composition of the disclosure (tranexamic acid, 500 mg/mL, pH 3-4) after IM administration of about 2 gram tranexamic acid to a subject, exhibits an Cmax in a range of from about 35 to about 47 ug/mL.

In some embodiments, the pharmaceutical composition of the disclosure (tranexamic acid, 500 mg/mL, pH 3-4) after IM administration of about 1 gram tranexamic acid to a subject, exhibits an Tmax in a range of from about 15 to about 120 minutes.

In some embodiments, the pharmaceutical composition of the disclosure (tranexamic acid, 500 mg/mL, pH 3-4) after IM administration of about 2 gram tranexamic acid to a subject, exhibits an Tmax in a range of from about 30 to about 60 minutes.

In some embodiments, the pharmaceutical composition of the disclosure (tranexamic acid, 500 mg/mL, pH 3-4) after IM administration of about 1 gram tranexamic acid to a subject, exhibits an AUCINF_pred in a range of from about 4800 to about 5500 min*μg/mL.

In some embodiments, the pharmaceutical composition of the disclosure (tranexamic acid, 500 mg/mL, pH 3-4) after IM administration of about 2 gram tranexamic acid to a subject, exhibits an AUCINF_pred in a range of from about 8000 to 9000 min*μg/mL.

In some embodiments, the pharmaceutical composition of the disclosure (tranexamic acid, 500 mg/mL, pH 3-4) after IM administration to a subject, exhibits an AUCINF_pred that is larger than that of commercial tranexamic acid (100 ug/mL, pH 6.5-8.0) following IV administration of a commercially available tranexamic acid injection in a similar dose.

Packaging

The pharmaceutical compositions of the disclosure can be packaged for use in a variety of pharmaceutically acceptable containers, for example, an aseptic container.

The pharmaceutically acceptable container may be associated with or suitable for use with a dispensing device. For example, pharmaceutical compositions of the disclosure can be stored in a pre-filled single dose dispensing device, or in an aseptic container that may be transferred to a dispensing device shortly before use. The term dispensing device may include without limitation auto-injectors, hypodermic syringes, micro needle syringes, micropumps, autoinjectors, jet injectors, topical dispensers, intradermal delivery devices, patch pumps, auricular dispensers, oral dispensers, eye droppers, infusers, pre-fillable syringes, pre-filled syringes, cartridges for pen injectors, cartridges for auto-injectors, or any other type of drug delivery device. For example, aseptic cartridges and dispenser arrangements are described in U.S. Pat. Nos. 9,820,913, 10,028,886, 10,864, 139, 10,981,713, and 11,001,435, each of which is incorporated herein by reference in its entirety.

Several existing products include a flexible package made from film or foils in which a product can be stored in an aseptic manner until the time of use. Some of these products further include a dispensing port communicating with the product in the dispensing package. In some cases, a rupturable barrier is presented between the port and the product to enhance the integrity of the package until the time of use. These flexible packages may comprise at least two product compartments that are mergeable prior to use to allow the substances from the different compartments to mix and form the dispensable product. In some cases, these packages are made from a film or a foil (together referred to as webs or web walls) where a first web wall is sealed to a second web wall to define the boundaries of a product compartment. These packages are sometimes referred to as bags, blisters, pouches, or sachets.

The pharmaceutically acceptable container may be a pouch, cartridge, reservoir, bag, blister, sachet, vial, or syringe. The pharmaceutically acceptable container may be a flexible primary container such as a pouch, cartridge, reservoir, bag, blister, or sachet for use in an auto-injector. In some embodiments, packages can be used that reduce the amount of light which can reach the composition. For example, in some embodiments, the container may, optionally, further comprise a light barrier, such as an aluminum embedded in the primary container's wall composition, aluminum overpouch, or a carton.

In some embodiments, the pharmaceutical compositions may be provided in any appropriate plastic container. The plastic container may be a flexible primary container. Any appropriate flexible primary container comprising an inert surface and/or providing moisture and oxygen barrier on par with glass may be employed. The flexible primary container may comprise a polymeric contact surface comprising cyclic olefin copolymer (COC), polypropylene (PP), high density polyethylene (HDPE), polychlorotrifluoroethylene (PCTFE), Barex (copolymer of acrylonitrile and methyl acrylate), Plexar resin (anhydride modified polyolefins), ethylene-vinyl alcohol (EVOH), polyethylene, polyolefin blend, polyvinyl chloride (PVC), ethylene-vinylacetate, and combinations such as polypropylene/Barex (copolymer of acrylonitrile and methyl acrylate), Plexar resin (anhydride modified polyolefins)/ethylene-vinyl alcohol (EVOH), COC (cyclic olefin copolymer)/EVOH, COC/HDPE, ethylene-propylene copolymer, or ethylene/propylene copolymer plastic containers.

In some embodiments, the pharmaceutical compositions may be packaged in a glass container. In some embodiments, the pharmaceutical compositions may be packaged in USP Type I borosilicate glass vials or USP Type II soda lime silica glass vials. The glass vials may be clear or amber glass vials. The glass vials may have a USP Elastomer Closure for Injections under <381> elastomeric stopper. The stopper may be selected from a butyl, EPDM, natural rubber, nitrile or silicone material. The butyl stopper may be selected from a chlorobutyl or bromobutyl stopper. The stopper or cap may be coated with a silicone, B2 crosslinked coating, Flurotec coating, Teflon coating, Westar RS treatment, RTS treatment, or thermoplastic elastomer (TPE) product. In some embodiments, the glass vial may be closed with a stopper and sealed with an aluminum cap.

Procedures for filling pharmaceutical compositions in pharmaceutically acceptable containers, and their subsequent processing are known in the art. These procedures can be used to produce sterile pharmaceutical drug products often required for health care. See, e.g., Center for Drug Evaluation and Research (CDER) and Center for Veterinary Medicine (CVM), "Guidance for Industry for the Submission Documentation for Sterilization Process Validation in Applications for Human and Veterinary Drug Products", (November 1994). Examples of suitable procedures for producing sterile pharmaceutical drug products include, but are not limited to, terminal moist heat sterilization, ethylene oxide, radiation (i.e., gamma and electron beam), and aseptic processing techniques. Any one of these sterilization procedures can be used to produce the sterile pharmaceutical compositions described herein.

In some embodiments, sterile pharmaceutical compositions can be prepared using aseptic processing techniques. Sterility may be maintained by using sterile materials and a controlled working environment. All containers and apparatus may be sterilized, preferably by heat sterilization, prior to filling. Then, the container may be filled under aseptic conditions, such as by passing the composition through a filter and filling the units. Therefore, the compositions can be sterile filled into a container to avoid the heat stress of terminal sterilization. In some embodiments, the compositions may be terminally sterilized using moist heat. Terminal sterilization can be used to destroy all viable microorganisms within the final, sealed container containing the pharmaceutical composition. An autoclave may be used to accomplish terminal heat-sterilization of drug products in their final packaging. Typical autoclave cycles in the pharmaceutical industry to achieve terminal sterilization of the final product may be performed at 121° C. for at least 10 minutes.

Auto-Injector Platform

One problem with respect to a TXA auto-injector product is the low solubility of TXA combined with the dose volume limitations of IM injections and current auto-injector designs.

An auto-injector was developed that can deliver up to a 5 ml dose and to address the shortfalls of current auto-injectors, including usability, robustness, drug stability, and manufacturing/quality complexities. Any appropriate auto-injector may be used to administer the pharmaceutical compositions according to the disclosure. For example, auto-injectors suitable for administration of the pharmaceutical compositions of the disclosure are disclosed in U.S. Pat. No. 10,716,901, which is incorporated herein by reference in its entirety.

In the auto-injector platform used in initial studies, the pharmaceutical compositions of the disclosure were stored in a glass-free flexible primary container as shown in FIG. 3A, improving product robustness and potentially drug stability. FIG. 3A shows a representative auto-injector arrangement with a single chamber configuration schematic showing the major components of the device. The auto-injector 300 is powered by a mini-$CO_2$ canister 330, which operates the needle 370 and collapses the flexible primary container 340 for delivery. The auto-injector body further houses a seal indicator 360, and includes an endpiece 310, shell 320, pressure chamber 350, aseptic cover 380, and cap 390. FIG. 3B shows an example of an auto-injector 305 with a dual chamber configuration, comprising a first flexible primary container 340 and a second flexible primary container 345. The auto-injector 305 additionally comprises a first needle 370 and a second needle 375. FIG. 4 shows a drawing of a representative auto-injector arrangement 400 with a single chamber configuration schematic including a visible endpiece 410, shell 420, flexible primary container 440, and cap 490.

FIG. 5A and 5B illustrate a ready-to-mix auto-injector arrangement 500 wherein reconstitution is triggered by rotation of a knob 523. FIG. 5A & FIG. 5B respectively illustrate cross-section views of the state of an auto-injector before & after reconstitution. The reconstitution mechanism 1 comprises a carriage associated to a cross member and a roller. The carriage further comprises a cam surface disposed against the corresponding cam surface of the activation knob 523. A follower 528 extends into a guide slot disposed against a rigid backing member abutting the flexible primary drug container 530. The container 530 may comprise a formed side which may be composed of a formed polymer providing a high barrier to fluid ingress. The container 530 may further comprise a lid side which may be of the same or different material, such as an aluminum backed polymer surface. A frangible seal provides a barrier to separate a first compartment 535, which may contain TXA or a pharmaceutically acceptable salt thereof in dry form as described, from a second compartment 536, which may contain a diluent such as water or a saline solution as described. In some variations a first compartment 535 may contain a diluent and a second compartment 536 may contain a dry active substance. A fitment may be configured to maintain the primary drug container 530 in place within the delivery device. The reconstituted chamber 539 maintains the reconstituted agent in a stored and sterile state. Depending on the particular mode and operation, arming of the device for dispensing may occur with reconstitution, as a subsequent action after a timed delay without further user input, or arming may only occur after further user input such as by removing a cap.

FIG. 5C illustrates a variation of a ready-to-mix reconstitution auto-injector arrangement 550 wherein reconstitution is triggered by rotation of the shell 511 of the injector body. The primary drug container 530 may comprise a formed side which may be composed of a formed polymer providing a high barrier to fluid ingress. The container 530 may further comprise a lid side which may be of the same or different material, such as an aluminum backed polymer surface. A frangible seal provides a barrier to separate a first compartment 535, which may contain TXA or a pharmaceutically acceptable salt thereof in dry form as described, from a second compartment 536, which may contain a diluent such as water or a saline solution as described. In some variations a first compartment 535 may contain a diluent and a second compartment 536 may contain a dry active substance. A reconstitution mechanism is disposed within the pressure chamber and may comprise a roller guide rod, a roller, and a roller harnessing strap which may be configured to loop around the roller and maintain its position. The reconstitution assembly may also comprise a roller retaining pin disposed within a hole in the harnessing strap and also within a stationary plate. The reconstitution mechanism may comprise a carriage, a linear bearing, a carriage guide rod, and carriage springs. Depending on the particular mode and operation, arming of the device for dispensing may occur with reconstitution, as a subsequent action after a timed delay without further user input, or arming may only occur after further user input such as by removing a cap.

The auto-injector comprising the TXA formulation of the disclosure exhibits extraordinary robustness far exceeding the military standard (MIL-STD) requirements. For example, the auto-injector platform used in initial studies has passed functional performance testing, including exposure to environmental pre-conditioning as per a plan based on MIL-STD-810G conditions, both exceeding these requirements and injecting through protective clothing materials.

Ergonomics of the auto-injector platform used in initial studies were optimized for the operational conditions and include large, clear label; tactile, audible and visual user feedback; and single-step, single-hand activation.

Other auto-injector configurations are possible including various features including a range of dose volumes up to 5 mL, injection through a single or multiple needles, simultaneous injections of multiple compounds through compound exclusive needles to prevent potential adverse effects resulting from mixing of drugs, and automatic reconstitution of dry compounds just prior to injection.

An auto-injector arrangement is provided comprising an auto-injector comprising an injector body housing a pharmaceutical composition according to the disclosure comprising tranexamic acid or a pharmaceutically acceptable salt thereof. In some embodiments, the injector body comprises a first compartment for storing the pharmaceutical composition, and optionally at least a second compartment for storing the pharmaceutical composition or at least one additional active agent separate from the pharmaceutical composition. In some embodiments, the optional additional active agent is selected from one or more of the group consisting of an anesthetic, analgesic, and antimicrobial agent.

An auto-injector arrangement is provided comprising an auto-injector comprising an injector body housing a ready-to-mix pharmaceutical composition comprising tranexamic acid or a pharmaceutically acceptable salt thereof. In some embodiments, the injector body comprises a first compartment for storing a ready-to-mix pharmaceutical composition comprising tranexamic acid or a pharmaceutically acceptable salt thereof, and at least a second compartment for storing aqueous diluent for the ready-to-mix pharmaceutical composition. When the aqueous diluent is mixed with the ready-to-mix composition, an injectable pharmaceutical composition according to the disclosure is formed having a pH of no more than about pH 5.0, or having a pH in a range of from about pH 3.0 to about pH 5.0, from about pH 3.0 to about 4.5, or from about pH 3.0 to about pH 4.0. The reconstituted pharmaceutical composition may be an intramuscular pharmaceutical composition according to the disclosure. In some examples, the reconstituted pharmaceutical composition comprises at least about 200 mg/mL of the tranexamic acid or pharmaceutically acceptable salt thereof, or in a range of from about 200 mg/mL to about 600 mg/mL, about 300 mg/mL to about 550 mg/mL, about 400 mg/mL to about 550 mg/mL, or about 475 mg/mL to about 425 mg/mL, or about 500 mg/mL of the tranexamic acid or pharmaceutically acceptable salt thereof.

The ready-to-mix composition comprising tranexamic acid or a pharmaceutically acceptable salts thereof may be in a dried form. The aqueous diluent may be any appropriate sterile diluent for injection known in the art. In some examples, the aqueous diluent may comprise a diluent selected from the group consisting of sterile water for injection, 0.9% sodium chloride for injection, 0.45% sodium chloride for injection, 0.5-5.0% benzyl alcohol, and sterile aqueous HCl in a range of pH 3 to about pH 5. The aqueous diluent may comprise at least 30 wt %, at least 40 w1%, at least 50 wt % water, at least 60 wt %, at least 70 wt % water. Optional additives to ready-to-mix composition and/or diluent may include an additive selected from the group consisting of pH adjuster, tonicity agent, anesthetic, buffer, solvent, preservative, carrier, and colorant.

In some embodiments, the injection is performed through a single needle. In some embodiments, the injection may be performed through multiple needles to adjacent depots in the muscle. In some embodiments, the auto-injector may comprise multiple needles as disclosed in U.S. patent application Ser. No. 16/933,779, US 2020-0345937, which is incorporated herein by reference in its entirety. Administering an injection through multiple needles creates multiple adjacent depots of the pharmaceutical composition in the muscle, increasing the area through which the pharmaceutical composition is absorbed, thereby reducing the amount of time needed to achieve therapeutic effects. Injection through multiple needles may additionally reduce stress on the target tissue and leakage out of the injection site to skin surface. Kits The disclosure provides a kit comprising an aseptic container comprising a pharmaceutical composition according to the disclosure and optionally a sheet of instructions or other form of instructions for use and labeling. The aseptic container may be a prefilled syringe. The aseptic container may be a prefilled pouch, cartridge, reservoir, vial, bag, blister, or sachet. The aseptic container may be a flexible primary container such as a pouch, cartridge, reservoir, bag, blister, a Blow-Fill-Seal package, or sachet for use in an auto-injector.

The kit may comprise a single auto-injector or a multiplicity of auto-injectors comprising a prefilled pouch, cartridge, reservoir, bag, blister, or sachet comprising a pharmaceutical composition according to the disclosure and optionally a sheet of instructions.

EXAMPLES

Example 1. Tranexamic Acid Compositions

Concentrated pharmaceutical compositions comprising tranexamic acid in solution at 500 mg/mL were developed. Two aqueous injectable solutions are provided comprising 500 mg/ml tranexamic acid in either (i) 0.9% normal saline, pH adjusted with HCl to ~pH 4, or (ii) 4% v/v benzyl alcohol in WFI, pH adjusted with HCl to ~pH 3-4. The compositions may be suitable for intramuscular injection.

Concentrated aqueous TXA formulations are shown in Tables 1, 2A and 2B.

Formulation A

Formulation A was 500 mg/ml TXA, 0.9% aq, sodium chloride, and pH 4.0. The TXA was dissolved in 4N HCl while stirring, the sodium chloride is added, add 4N HCl to achieve desired pH, q.s. with WFI. The pH of Formulation A was 4.0. Formulation A is shown in Table 1.

TABLE 1

| Formulation A | |
| --- | --- |
| Ingredient | Formulation per 1.0 mL |
| Tranexamic acid | 500 mg |
| Sodium chloride | 9.0 mg |
| 4N HCl | q.s. pH 3-4 |
| Water for injection | Ad 1.0 mL |

Formulation B

Formulation B was 500 mg/mL TXA, 4% aq. benzyl alcohol, pH 3.0-4.0. The following procedure was developed for the preparation of 100 mL formulation B and may be scaled as necessary. Measure 50 g TXA on a weigh boat and record exact weight. Add to a formulation flask through powder funnel. Add 25 mL 4N HCl to flask with stirring. Begin heating flask to aid TXA dissolution. Measure 4.0 mL benzyl alcohol into class A graduated cylinder and add to formulation. While heating and stirring the formulation, continue to add 4NHCl to the flask in 5 mL aliquots until the TXA had dissolved record the amount of HCl added. When the TXA has dissolved, q.s. with WFI in class A volumetric flask. The pH of Formulation B was pH 3.0-4.0. Formulation B is shown in Table 2A.

TABLE 2A

| Formulation B | |
| --- | --- |
| Ingredient | Formulation per 1.0 mL |
| Tranexamic acid | 500 mg |
| Benzyl alcohol | 0.04 mL |
| 4N HCl | q.s. pH 3-4 |
| Water for injection | Ad 1.0 mL |

Formulation C

Formulation C was 500 mg/mL TXA, pH 3.0-4.0. The following procedure was developed for the preparation of 100 mL formulation C and may be scaled as necessary. Measure 50 g TXA on a weigh boat and record exact weight. Add to a formulation flask through powder funnel. Add 25 mL 4N HCl to flask with stirring. Begin heating flask to aid TXA dissolution. While heating and stirring the formulation, continue to add 4N HCl to the flask in 5 mL aliquots until the TXA had dissolved record the amount of HCl added.

When the TXA has dissolved, q.s. with WFI in class A volumetric flask. The pH of Formulation C was pH 3.0-4.0. Formulation C is shown in Table 2B.

TABLE 2B

| Formulation C | |
| --- | --- |
| Ingredient | Formulation per 1.0 mL |
| Tranexamic acid | 500 mg |
| 4N HCl | q.s. pH 3-4 |
| Water for injection | Ad 1.0 mL |

500 units of the TXA auto-injector prototype were produced for an array of functional performance tests and for use in the animal studies.

Example 2. Stability Studies

Stability studies of TXA Formulation A (aq. TXA 500 mg/mL, 0.9% NaCl, pH 3-4) and Formulation B (aq. TXA, 4% benzyl alcohol, pH 3-4) are ongoing and the most recent 15-month timepoint shows complete drug recovery and no change in pH at room temperature (25° C.±2° C./60%±5% RH) and in accelerated storage conditions (40° C.±2° C./75%±5% RH). Stability testing is being performed by using HPLC and pH assays.

Various containers comprising flexible plastic PDC materials provide moisture and oxygen barrier on par with glass were evaluated.

Table 3 and Table 4 show pH stability of comparative 100 mg/mL tranexamic acid injection (starting pH 7.5) and test Formulation A (starting pH 4.0) compositions, respectively, when stored over 6 months in glass control vial, or three plastic flexible containers at room temperature (25° C.±2° C./60%±5% RH) and in accelerated storage conditions (40° C.±2° C./75%±5% RH). The containers were constructed of two sheets of film joined together along their periphery, forming a cavity therebetween. Container Types 1 and 3 were constructed from two different film materials, whereas Container Type 2 used only one film material.

Container Type 1: copolyester/EVOH/PCTFE film and PET/aluminum/BOPET film

Container Type 2: polyolefin/aluminum/nylon film

Container Type 3: polyolefin/aluminum/nylon film and PET/aluminum/BOPET film

TABLE 3

| 100 mg/mL Comparative Tranexamic Acid Injection pH Stability pH 7.0 | | | | | | | | |
| --- | --- | --- | --- | --- | --- | --- | --- | --- |
| Container Type | t = 0 | t = 7 days (25° C./ 60% RH) | t = 1 month (40° C./ 75% RH) | t = 2 months (25° C./ 60% RH) | t = 3 months (25° C./ 60% RH) | t = 3 months (40° C./ 75% RH) | t = 6 months (25° C./ 60% RH) | t = 6 months (40° C./ 75% RH) |
| Control | 7.53 | 7.36 | 7.50 | 7.53 | 7.53 | 7.50 | 7.45 | 7.42 |
| Vial | 7.50 | 7.40 | 7.51 | 7.54 | 7.53 | 7.52 | 7.45 | 7.42 |
| Type 1 | na | 7.40 | 7.38 | 7.36 | 7.38 | 7.31 | 7.27 | 7.16 |
| | na | 7.40 | 7.37 | 7.37 | 7.35 | 7.33 | 7.28 | 7.18 |
| Type 2 | na | 7.44 | 7.40 | 7.45 | 7.49 | 7.41 | 7.32 | 7.31 |
| | na | 7.44 | 7.41 | 7.44 | 7.42 | 7.39 | 7.37 | 7.29 |
| Type 3 | na | 7.43 | 7.35 | 7.47 | 7.46 | 7.30 | 6.97 | 7.19 |
| | na | 7.41 | 7.33 | 7.44 | 7.40 | 7.32 | 7.37 | 7.18 |

TABLE 4

| 500 mg/mL Test Tranexamic Acid Injection pH Stability pH 4.0 | | | | | | | | |
| --- | --- | --- | --- | --- | --- | --- | --- | --- |
| Container Type | t = 0 | t = 7 days (25° C./ 60% RH) | t = 1 month (40° C./ 75% RH) | t = 2 months (25° C./ 60% RH) | t = 3 months (25° C./ 60% RH) | t = 3 month (40° C./ 75% RH) | t = 6 months (25° C./ 60% RH) | t = 6 month (40° C./ 75% RH) |
| Control | 4.01 | 3.87 | 3.97 | 3.94 | 3.93 | 3.92 | 3.70 | 3.65 |
| Vial | 4.02 | 3.89 | 3.91 | 3.99 | 3.93 | 3.94 | 3.75 | 3.70 |
| Type 1 | na | 3.90 | 3.99 | 3.99 | 3.98 | 3.94 | 3.57 | 3.51 |
| | na | 3.90 | 3.93 | 4.01 | 3.95 | 3.98 | 3.69 | 3.64 |
| Type 2 | na | 3.83 | 3.94 | 3.95 | 3.98 | 3.94 | 3.47 | na |
| | na | 3.87 | 3.94 | 3.97 | 3.96 | 3.97 | 3.60 | na |
| Type 3 | na | 3.84 | 3.96 | 3.87 | 4.04 | 3.94 | 3.54 | 3.64 |
| | na | 3.90 | 3.97 | 3.99 | 3.96 | 3.96 | 3.65 | na |

As shown in Table 4, 500 mg/ml Test Trapexamic Acid Injection Formulation A: maintained a pH within about 10.5 points compared to starting pH 4.0 over at least 6 months when stored in control glass vial, or three types of flexible plastic containers at room temperature (25° C./60% RH) or at accelerated storage conditions (40° C./75% RH).

Tables 5 and 6 show tranexamic acid concentration by HPLC of comparative 100 mg/mL tranexamic acid injection (starting pH 7.5) and test 500 mg/mL Test Tranexamic Acid Injection Formulation A (starting pH 4.0) compositions when stored over 6 months in glass control vial, or three flexible plastic containers at room temperature (25° C.±2° C./60%±5% RH) and in accelerated storage conditions (40° C.±2° C./75%±5% RH).

detector collecting spectrum from 200 to 400 nm. The peak purity is assessed at 270 nm, including the upslope and downslope. The drug substance, drug product, placebo, and the marketed TXA drug product will be subjected to heat, light, acid, base, and oxidative stress conditions.

Example 3. Pre-Clinical Pharmacokinetic Studies in Swine

Studies of pharmacokinetics (PK) and pharmacodynamics (PD) of TXA were performed in swine conducted in compliance with Good Laboratory Practice (GLP) standards. All facilities and activities were accredited in accordance with GLP and ISO9001 (2015). The purpose of this study was to

TABLE 5

| | | 100 mg/mL Tranexamic Acid Injection HPLC Stability pH 7.0 | | | | | | |
|---|---|---|---|---|---|---|---|---|
| Container Type | t = 0 | t = 7 days (25° C./ 60% RH) | t = 1 month (40° C./ 75% RH) | t = 2 months (25° C./ 60% RH) | t = 3 months (25° C./ 60% RH) | t = 3 months (40° C./ 75% RH) | t = 6 months (25° C./ 60% RH) | t = 6 months (40° C./ 75% RH) |
| Control | 99.90% | 101.50% | 101.30% | 101.00% | 102.20% | 105.30% | 100.60% | 100.80% |
| Vial | 99.90% | 100.60% | 100.70% | 100.70% | 102.70% | 103.20% | 101.00% | 101.10% |
| Type 1 | na | 101.40% | 99.40% | 101.50% | 103.20% | 102.90% | 100.10% | 101.30% |
| | na | 101.10% | 101.00% | 100.70% | 102.50% | 103.20% | 100.20% | 102.00% |
| Type 2 | na | 100.00% | 100.10% | 101.30% | 102.00% | 104.30% | 101.60% | 116.90% |
| | na | 101.00% | 99.90% | 100.30% | 102.10% | 103.40% | 100.80% | 115.70% |
| Type 3 | na | 100.10% | 100.10% | 99.50% | 102.40% | 101.90% | 101.30% | 99.90% |
| | na | 101.10% | 100.90% | 100.50% | 101.90% | 105.20% | 100.90% | 102.70% |

TABLE 6

| | | 500 mg/mL Tranexamic Acid Injection HPLC Stability pH 4.0 | | | | | | |
|---|---|---|---|---|---|---|---|---|
| Container Type | t = 0 | t = 7 days (25° C./ 60% RH) | t = 1 month (40° C./ 75% RH) | t = 2 months (25° C./ 60% RH) | t = 3 months (25° C./ 60% RH) | t = 3 month (40° C./ 75% RH) | t = 6 months (25° C./ 60% RH) | t = 6 month (40° C./ 75% RH |
| Control | 99.50% | 100.90% | 100.40% | 100.20% | 102.10% | 102.20% | 100.60% | 101.00% |
| Vial | 99.50% | 100.40% | 100.30% | 100.50% | 102.40% | 102.50% | 100.80% | 100.80% |
| Type 1 | na | 101.30% | 100.20% | 100.50% | 102.50% | 102.60% | 100.90% | 101.10% |
| | na | 101.10% | 100.30% | 100.80% | 102.70% | 102.40% | 101.00% | 101.30% |
| Type 2 | na | 100.30% | 100.50% | 99.80% | 102.20% | 102.90% | 101.40% | na |
| | na | 100.30% | 100.60% | 100.00% | 102.20% | 102.40% | 101.00% | na |
| Type 3 | na | 100.10% | 100.90% | 100.10% | 101.90% | 102.20% | 99.90% | 100.40% |
| | na | 100.50% | 101.10% | 99.90% | 102.00% | 101.50% | 100.50% | na |

As shown in Table 6, Test Formulation A maintained a concentration of tranexamic acid within ±4% of the starting concentration by HPLC over at least six months when stored over 6 months in glass control vial, or three types of flexible plastic containers at room temperature (25° C.±2° C./60%±5% RH) and in accelerated storage conditions (40° C.±2° C./75%±5% RH).

Impurities (substances other than active pharmaceutical ingredients and excipients) and their levels in the new formulation of TXA are identified and compared against the impurities in the reference listed drug (RLD) according to the International Council for Harmonisation of Technical Requirements for Pharmaceuticals for Human Use (ICH) Q3A(R), Q3B(R), and Q3C(R) requirements for impurities in drug substances and drug products. Impurities will be identified in the new TXA formulations and the commercial product in forced degradation studies.

Forced degradation studies are designed to assess the impurities in the new formulation of TXA. Forced degradation studies are conducted using HPLC and a diode-array evaluate the PK and PD of TXA in domestic pigs' plasma, following IV and IM administration of different concentrations and dosages of TXA.

Eighteen domestic pigs were assigned to four test groups. Group 1: Control, IM administered with vehicle (0.9% NaCl, pH 3-4, w/v), two animals were administered 2 mL vehicle, one animal administered 4 mL vehicle. Group 2: Reference, IV administered TXA (5 animals received 10 mL of 100 mg/mL solution of total dosage of 1 g TXA (TRANEX injection) injected over 10 min period, approximately 1 mL every minute). Group 3: IM administered TXA bolus injection (5 animals received 2 mL of 500 mg/mL solution, pH 3-4, providing total dose of 1 g TXA dissolved in vehicle. Group 4: IM administered with TXA bolus injection (5 animals received 4 mL of 500 mg/ml, solution, pH 3-4, for total dose of 2 g TXA dissolved in vehicle).

The PK/PD and safety study was performed in swine and compared the marketed TXA product (100 mg/mL, pH 6.5-8.0, 10 mL IV) against the formulation A (TXA 500 mg/mL, pH 3-4, 2 mL, IM) of the disclosure at the standard TXA dose used for pre-hospital hemorrhage treatment (1 gram). Test groups included: 1gr commercial TXA IV, 1gr TXA formulation A IM, 2gr TXA formulation A IM, and saline IM control. IM injections were performed using an auto-injector. Blood was collected over a period of 72 hours for determination of TXA levels and for CBC, blood biochemistry, PT/PTT and TEG analysis. PK analysis was noncompartmental. Following sacrifice, animals were subjected to a full detailed necropsy and histopathological evaluation performed on injection sites and major organs.

Blood was collected from all animals for TXA PK analysis at the following timepoints: baseline (no more than 5 minutes prior to dosing), 1, 5, 10, 15, 20, 30, 45 minutes and 1, 2, 3, 4, 6, 8, 12, 24 and 72 hours post dosing. Additional blood samples were collected for Complete Blood Count (CBC), biochemistry profile and prothrombin time/partial thromboplastin time (PT/PTT) at baseline, 1, 3, and 72 hr post dosing. For thromboelastographic (TEG) analysis blood was collected at base line, 1, 3 and 6 hr post dosing. The study was conducted over 5 separate dosing sessions. For each session the animals were acclimatized for at least 4 days prior to Central Venous Catheter (CVCs) placement procedure. All animals were sacrificed 72 hours post treatment and were subjected to a full gross necropsy. Organ samples and injection sites were collected for histopathological analysis.

Pharmacokinetic and bioanalytical analysis of Tranexamic acid, based on plasma samples, was performed. On the date of analysis, plasma samples were thawed at room temperature, along with calibration and QC samples. 50 μL of plasma were taken for analysis. Tranexamic acid and its internal standard were separated from pig plasma by protein precipitation. The samples were analyzed by a validated high-performance liquid chromatography-mass spectrometry/mass spectrometry (HPLC-MS/MS) method, using Hilic Silica 3 μm column with an electro-spray interface, in a positive ion mode.

Results:

No treatment related mortality occurred during the study. No significant abnormal clinical signs were observed throughout the observation period. All clinical signs were expected following central venous catheter (CVC) insertion, performance of bleeding and IM injection of an acidic solution. No discernable weight changes associated with administration of the Test, Control and Reference materials were detected.

CBC Analysis

For CBC analysis while blood was collected into commercial EDTA K3 tubes. Kept at 2-8 C for no more than 24 h, packed in ice pack, and transported to test site. Hematology White Blood Cell (WBC) levels of Test Groups 3 and 4 (IM administration) were not statistically significant different that those of Test Group 2 (IV administration). Hemoglobin (HGB) levels, Hemoglobin (HGB) levels, and Hematocrit (HCT) levels were within the normal ranges in all animals throughout the study. In comparison of baseline, Platelets levels to 72 hr levels, no significantly different was observed.

Blood Biochemistry

Blood biochemistry analysis was performed using ROCHE-COBAS 6000 C501

Analyzer on samples obtained at baseline and at 1hr, 3 hr and 72 hr post dosing. Total Bilirubin levels observed throughout the study were within normal ranges, except for slightly elevated total bilirubin levels compared to normal, which were observed in two animals, at baseline. In comparison to baseline, Alkaline Phosphatase levels at 72 hr, in all groups, were significantly lower (p<0.05, T test). In comparison to baseline, Aspartate aminotransferase (SGOT, AST) levels were significantly lower at 72 hr, in comparison to baseline levels, in Group 2 (p=0.0002, T test) and Group 4 (p=0.01, T test). Elevated levels of Alanine Transaminase (SGPT, ALT compared to normal range), were obtained at different timepoints in several animals. In Group 2, SGPT levels were significantly lower at 72 hr, in compression to baseline levels, (p=0.04, T TEST). Elevated levels of Gamma Glutamyl Transpeptidase (GGTP, compared to normal range), were obtained at different timepoints in several animals. In Group 4, GGTP levels were significantly lower at 72 hr, in compression to baseline levels (p=0.05, T TEST). Blood chemistry changes from normal ranges were deemed to be a result of the surgical procedure and anesthesia administrated during CVC insertion (performed one day prior to dosing).

Kidney Function

The kidney function main parameters evaluated included serum creatinine and urea as evaluated using ROCHE-COBAS 6000 C501 analyzer were within normal levels almost without exception, such that administration of control (Group 1), reference (Group 2) and test items (Groups 3 and 4) were deemed to have no effect on kidney function.

Coagulation Analysis

Prothrombin time (PT) and activated Partial Thromboplastin Time (PTT) analysis using Sysmex CA-1500 showed no significant differences between baseline levels and those seen at 72 hr post dosing.

TEG Analysis

When TXA is given to treat a condition of traumatic hemorrhage, it decreases the conversion of plasminogen to plasmin, preventing fibrin degradation and preserving the framework of fibrin's matrix structure. Therefore, when thromboelastographic (TEG) analysis is performed on blood collected before and after TXA administration, an effect on the Lys30 parameter may be exhibited. For TEG analysis approximately 6 mL whole blood was collected in commercial citrate tubes and loaded into TEG®5000 Hemostasis analyzer system immediately after collection. Lys30 is the percentage of clot which lysed after 30 minutes (after maximum clot strength). Comparison of Lys30 1hr and 6 hr levels to baseline levels, within all test groups, showed no significant differences. This may be explained considering the fact that in this PK study, no hemorrhage was induced.

Non-Compartmental Analysis (NCA)

Figure 6:
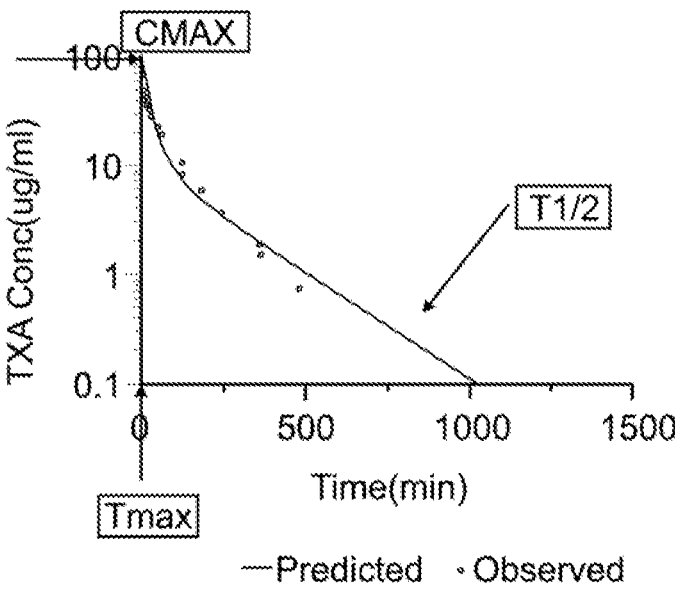
FIG. 6 shows a graph of average TXA plasma concentration over time in swine reference Group 2, IV administered TXA (TRANEX injection). 5 animals each received 10 mL of 100 mg/mL solution of total dosage of 1 g TXA injected over 10 min, pH 6.5-8.
Figure 7:
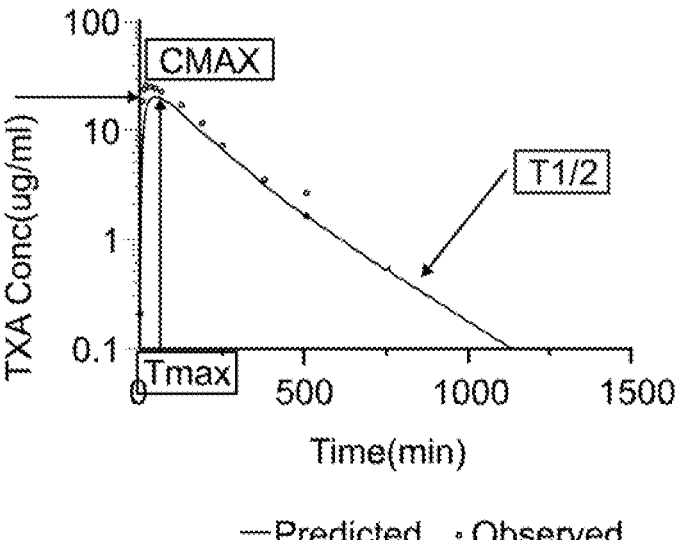
FIG. 7 shows a graph of average TXA plasma concentration over time in swine test Group 3: IM administered TXA. S animals each received 2 mL of 500 mg/ml, solution providing total dose of 1 g TXA dissolved in vehicle, pH 3-4.
Figure 8:
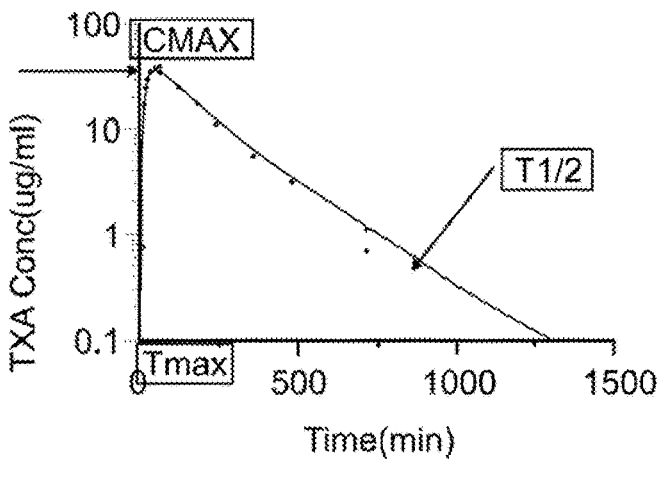
FIG. 8 shows a graph of average TXA plasma concentration over time in swine test Group 4: IM administered TXA. 5 animals each received 4 mL of 500 mg/mL solution for total dose of 2 g TXA dissolved in vehicle, pH 3-4.

Mean TXA plasma concentration over time for Groups 2, 3 and 4 are shown in FIGS. 6, 7 and 8, respectively.

Figure 9:
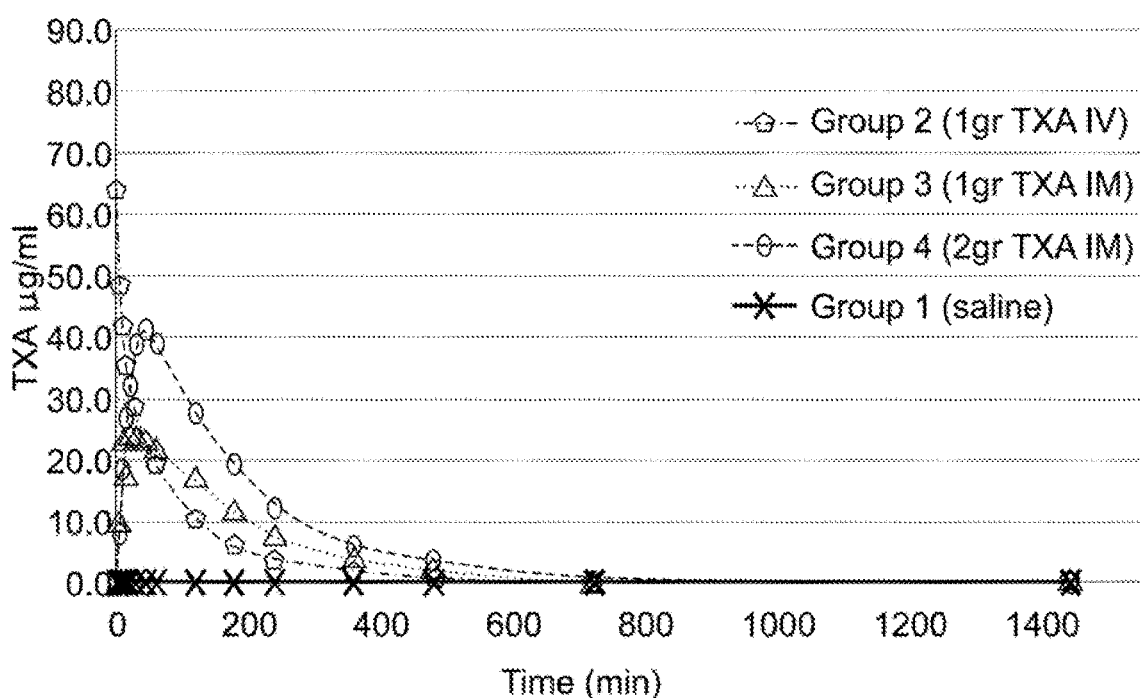
FIG. 9 shows a graph of TXA mean plasma concentration over time in all 4 Groups including Group I (saline control IM, n=3), Group 2 (1 gr TXA IV, n=5), Group 3 (1 gr TXA IM, n=5), and Group 4 (2 gr TXA IM, n=5). In Group 2, after 1 min from end of 10 min IV injection of 1 gr TXA, the drug reached a mean peak plasma concentration of 64 μg/mL. In 1 gr TXA IM Group 3, the drug reached a mean peak plasma concentration of 24.2 μg/mL within 20 min post dosing. In 2 gr TXA IM Group 4, the drug reached a mean peak plasma concentration of 41 μg/mL within 45 min post dosing.

FIG. 9 shows a graph of TXA mean plasma concentration over time in all 4 Groups including Group 1 (saline control IM, n=3), Group 2 (1 gr TXA IV, n=5), Group 3 (1 gr TXA IM, n=5), and Group 4 (2 gr TXA IM, n=5). In Group 2, after 1 min from end of 10 min IV injection of 1 gr TXA, the drug reached a mean peak plasma concentration of 64 ug/mL. In 1 gr TXA IM Group 3, the drug reached a mean peak plasma concentration of 24.2 μg/mL within 20 min post dosing. In 2 gr TXA IM Group 4, the drug reached a mean peak plasma concentration of 41 μg/mL within 45 min post dosing.

Figure 10:
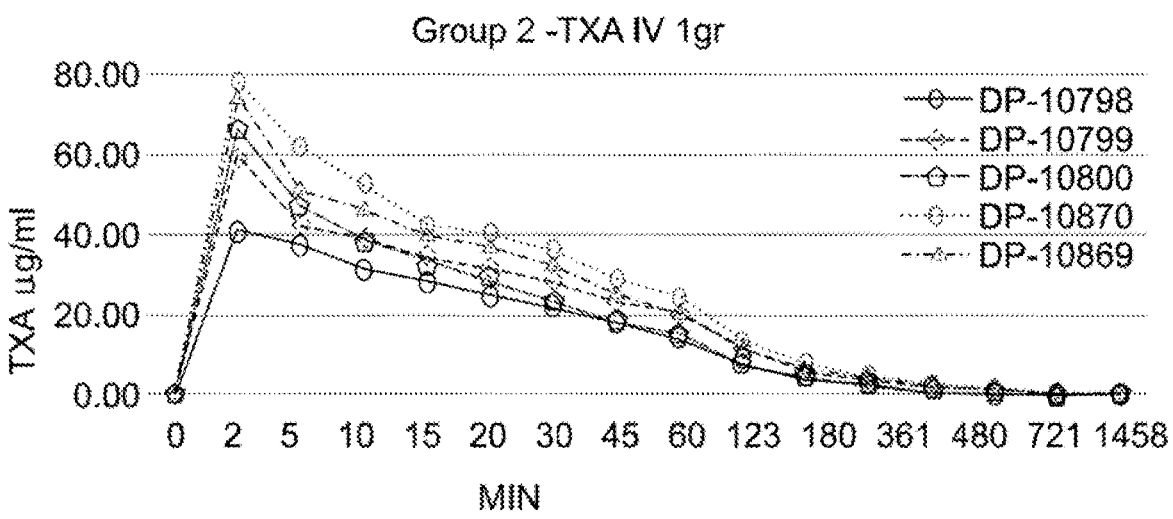
FIG. 10 shows a graph of individual pig TXA plasma concentration (ug/mL) over time for Group 2 animals (n=5) receiving 1 g IV TXA (100 ug/mL, pH 6.5-8.0, 10 mL) after end of 10 min IV infusion.
Figure 11:
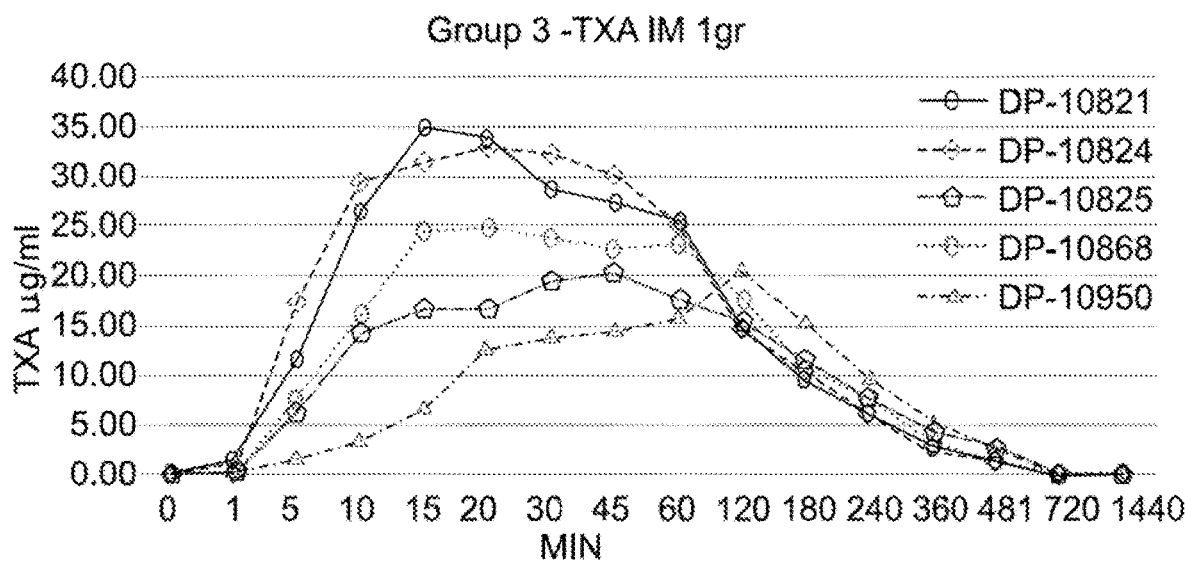
FIG. 11 shows a graph of individual pig TXA plasma concentration (ug/mL) over time for Group 3 animals (n=5) receiving 1 g IM TXA (500 ug/mL, pH 6.5-8.0, 2 mL) after IM TXA bolus administration.
Figure 12:
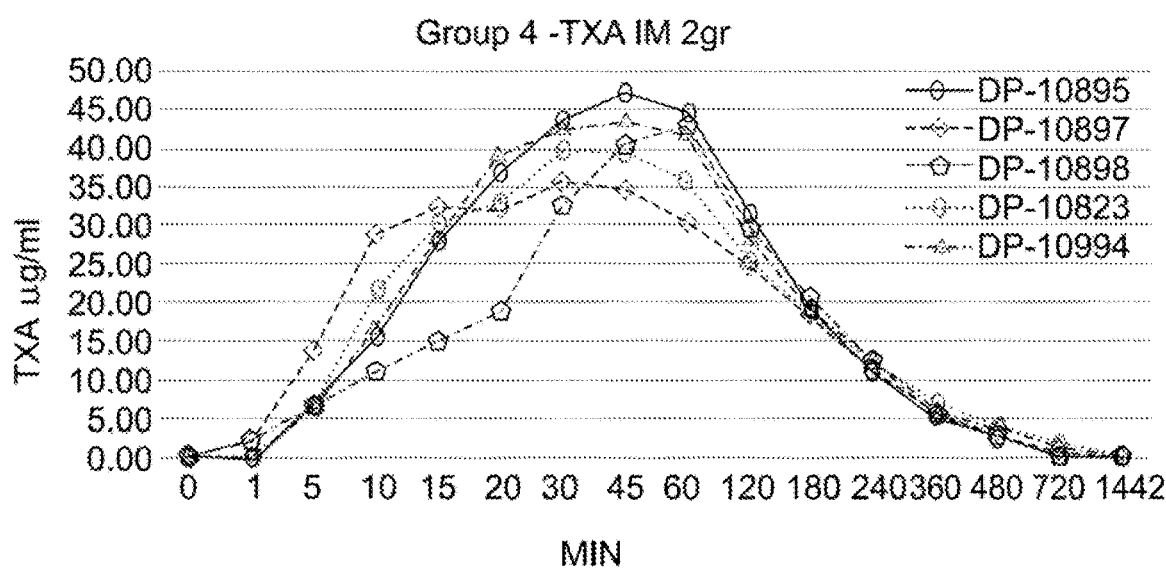
FIG. 12 shows a graph of individual pig TXA plasma concentration (ug/mL) over time for Group 4 animals (n=5) receiving 2 g IM TXA (500 ug/mL, pH 6.5-8.0, 4 mL) after IM TXA bolus administration.

Bioanalytical analysis of TXA concentration in the individual animal's plasma in each of Group 2, Group 3, and Group 4 are illustrated in in FIGS. 10, 11 and 12, respectively. The 3 animals in Group 1 (IM, saline) exhibited TXA concentration below lowest limit of quantitation (BLQ) (<1.015 ug/mL TXA) at each time point, data not shown.

In NCA evaluation using the Phoenix Winnonlin software, significant differences in the mean peak plasma concentration (Cmax) between the three groups; group 2 (administrated with 1gr TXA, IV) reached mean Cmax of 63.96 µg/mL, while group 3 (administrated with 1gr TXA, IM) mean Cmax was 26.63 µg/mL and group 4 (administrated with 2gr TXA, IM) mean Cmax reached 41.83 µg/mL (p<0.01, ANOVA). Group 2 Cmax ranged from 40.86 to 78.48 ug/mL (n=5). Group 3 Cmax ranged from 20.10 to 34.84 ng/mL (n=5). Group 4 Cmax ranged from 35.67 to 46.98 ug/ml (n=5).

Time at the peak observed concentration (Tmax) evaluation showed that group 2 mean Tmax was 11.2 minute, and group 3 and 4 mean Tmax, were 44 and 41.8 minutes respectively, as predicted from comparison between IV and IM drug administration, Tmax was longer for the IM administrated groups due to longer absorption time. Group 2 Tmax ranged from 11-12 min (n=5). Group 3 Tmax ranged from 15-120 min (n=5). Group 4 Tmax ranged from 30-60 min (n=5).

Comparison of the AUC (t=0 to infinity) showed significant differences between the three groups. Group 2 exhibited mean AUCINF_pred of 1gr TXA administrated IV was 4440.36, min*µg/mL (n=5). Group 3 exhibited mean AUCINF_pred of TXA administrated IM was 5086.07 min*µg/mL for 1gr TXA (n=5, range 4888.23 to 5417.10 min*µg/mL). Group 4 exhibited mean 8454.72 min*µg/ml for 2gr TXA (p<0.01, ANOVA) (n=5, range 8056.65 to 8858.21 min*µg/mL). Bioavailability calculation of the IM administrated TXA, suggests that the bioavailability is larger than 1 for group 3 administrated IM with 1gr of TXA.

Bioavailability calculation shows that the AUC for the dose of 1gr IM is larger in average than the corresponding one for the IV group (similar dose). In comparison of the 1gr and 2gr IM administrated groups, the NCA results demonstrate that TXA, when administrated IM, exhibits dose proportionality.

Figure 13:
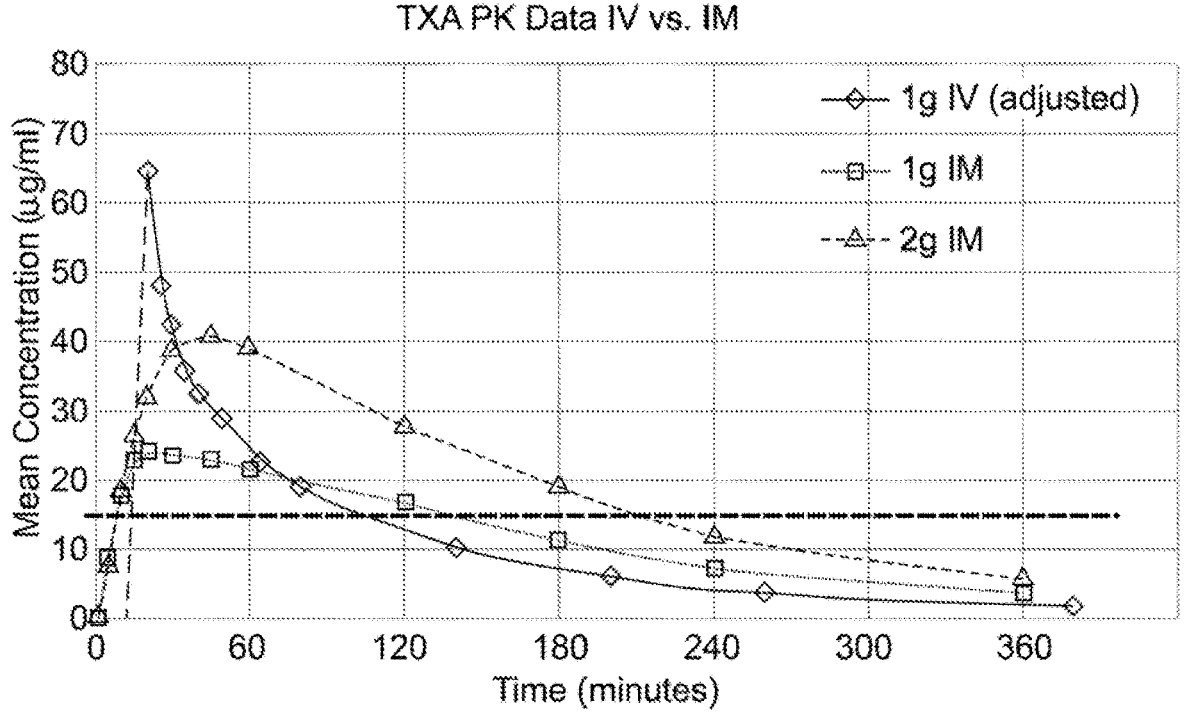
FIG. 13 shows a graph of mean TXA plasma concentration (ug/mL) vs. time following IV or IM administration in swine. Group 2 IV administration of 1 g TXA is shown as diamonds, Group 3 IM administration of 1 g TXA is shown as squares, and Group 4 IM administration is shown as triangles. The horizontal dotted line indicates an accepted minimum target TXA plasma level for inhibition of hyperfibrinolysis of about 15 ug/mL (effective TXA concentration). IM administration maintains effective TXA levels for inhibition of hyperfibrinolysis longer (>~130 min) than IV administration (<~105 min). IM administration also has the advantage of avoiding the high TXA concentrations of IV administration that are more likely to result in undesirable side effects.

FIG. 13 shows a graph of TXA pK data following IV or IM administration showing mean plasma concentration (ug/mL) vs. time. Group 2 IV administration of 1 g TXA is shown as diamonds, Group 3 IM administration of 1 g TXA is shown as squares, and Group 4 IM administration is shown as triangles. The horizontal dotted line indicates the widely accepted target TXA plasma level for inhibition of hyperfibrinolysis of about 10 to about 15 ug/ml (effective TXA concentration). For example, a systemic review of in vitro and in vivo pharmacodynamics studies found TXA concentrations in blood or plasma between 10 and 15 mg/L (10-15 ug/mL) results in substantial inhibition of fibrinolysis. (Picetti et al., 2019, Blood Coagulation and Fibrinolysis 2019, 30:1-10).

As shown in FIG. 13, IM administration maintains effective TXA levels for inhibition of hyperfibrinolysis longer than IV. As shown, 1 g IV TXA administration results in about 80 minutes of effective plasma concentration. In contrast 1 g IM TXA administration results in about 130 minutes of effective plasma concentration. 2 g IM TXA administration results in about 200 minutes of effective plasma concentration.

IM administration also has the advantage of avoiding the high TXA concentrations of IV administration that are more likely to result in undesirable side effects. In FIG. 13, the IV curve is adjusted (i.e., shifted right) to account for the time needed to place an IV line in field conditions (10 min), and to complete the TXA IV drip (10 min). The IV trace begins with a dashed line when the IV drip begins, at the 10 minute timepoint-no samples are taken during this time and the dashed line represents an estimation of increasing blood levels of TXA. The first data point is taken after completing the drip, at the 20 minute timepoint, where the trace starts being drawn as a solid line.

Example 4. Efficacy Study of TXA in a Controlled Hemorrhage Model in Swine

A GLP Efficacy study of TXA in a Controlled Hemorrhage Model in Swine was designed. The study design evaluates effectiveness of TXA at a single dose (1 g) in a controlled hemorrhage model in swine, comparing IM administration (TXA 500 mg/mL, ~pH 4.0) with an auto-injector against IV administration (TXA 100 mg/mL, pH 6.5-8.0).

Efficacy will be evaluated in a controlled model of hemorrhage in swine, along with the same PK/PD and safety parameters as in naïve swine. Given the wealth of clinical and animal data on TXA safety and efficacy in treating hemorrhage and on the IM route of TXA administration, results of the study will be used for dose selection, and determination of data collection timepoints.

The above specification, examples and data provide a complete description of the manufacture and use of the composition of the invention. Since many embodiments of the invention can be made without departing from the spirit and scope of the invention, the invention resides in the claims hereinafter appended.

CLAUSES

Clause 1. A ready-to-use injectable pharmaceutical composition comprising a therapeutically effective amount of tranexamic acid or a pharmaceutically acceptable salt thereof, the composition having a pH of no more than about pH 5.0, optionally wherein the ready-to-use injectable pharmaceutical composition is an aqueous composition.

Clause 2. The pharmaceutical composition according to clause 1, having a pH in a range of from about pH 3.0 to about pH 5.0, from about pH 3.0 to about pH 4.5, or from about pH 3.0 to about pH 4.0.

Clause 3. The pharmaceutical composition according to clause 1 or 2, comprising at least about 200 mg/mL of the tranexamic acid or pharmaceutically acceptable salt thereof.

Clause 4. The pharmaceutical composition according to any one of clauses 1 to 3, comprising from about 200 mg/mL to about 600 mg/mL, about 300 mg/mL to about 550 mg/mL, about 400 mg/mL to about 550 mg/mL, about 450 mg/mL to about 550 mg/mL, about 475 mg/mL to about 525 mg/mL, or about 400 mg/mL, about 425 mg/mL, about 450 mg/mL, about 475 mg/mL, about 500 mg/mL, about 525 mg/mL, about 550 mg/mL, about 575 mg/mL, or about 600 mg/mL of the tranexamic acid or pharmaceutically acceptable salt thereof in solution.

Clause 5. The pharmaceutical composition according to any one of clauses 1 to 4, wherein the composition is an aqueous solution that requires no dilution before administration.

Clause 6. The pharmaceutical composition according to any one of clauses 1 to 5, comprising one or more additives selected from the group consisting of pH adjuster, tonicity agent, anesthetic, buffer, solvent, preservative, carrier, and colorant.

Clause 7. The pharmaceutical composition according to clause 6, wherein the pH adjuster is hydrochloric acid.

Clause 8. The pharmaceutical composition according to clause 6 or 7, wherein the tonicity agent is selected from the group consisting of sodium chloride, glycerin, mannitol, dextrose, and trebalose.

Clause 9. The pharmaceutical composition according to clause 8, having a tonicity in a range of between about 270 to about 340 mOsm/kg.

Clause 10. The pharmaceutical composition according to any one of clauses 6 to 9, wherein the anesthetic is benzyl alcohol.

Clause 11. The pharmaceutical composition according to any one of clauses 6 to 10, wherein the solvent is selected from the group consisting of ethyl alcohol, isopropyl alcohol, methanol, polyethylene glycol, propylene glycol, benzyl benzoate, dimethyl sulfoxide, dimethyl formamide, acetone, acetonitrile, butanone, and solketal.

Clause 12. The pharmaceutical composition according to any one of clauses 6 to 11, wherein the carrier is selected from an albumin, and a cyclodextrin.

Clause 13. The pharmaceutical composition according to any one of clauses 1 to 12, wherein the composition does not include liposomes.

Clause 14. A pharmaceutical composition for parenteral administration comprising a ready-to-use aqueous solution with a pH in a range of from about pH 3.0 to about pH 5.0 comprising: from 300 to about 600 mg/mL tranexamic acid or a pharmaceutically acceptable salt thereof; and a pH adjuster in an amount to provide initial pH from about pH 3.0 to about pH 5.0.

Clause 15. The pharmaceutical composition according to clause 14, having a pH in a range of from about 3 to about 4.5, or about 3.0 to about 4.0, comprising: from about 450 to about 550 mg/mL tranexamic acid or a pharmaceutically acceptable salt thereof; and a pH adjuster in an amount to provide initial pH from about 3.5 to about 4.5.

Clause 16. The pharmaceutical composition according to clause 14 or 15, further comprising a tonicity agent, optionally wherein the tonicity agent is about 0.9% (w/v) sodium chloride.

Clause 17. The pharmaceutical composition according to any one of clauses 14 to 16, further comprising from about 2% to about 6%, about 3% to about 5%, or about 3.5% to about 4.5% (v/v) benzyl alcohol.

Clause 18. The pharmaceutical composition according to any one of clauses 14 to 17, wherein the composition requires no dilution before administration.

Clause 19. The pharmaceutical composition according to any one of clauses 1 to 18, wherein the composition when stored for 6 months at 25° C. at 60% relative humidity (RH) is capable of maintaining: a pH within about ±0.5 points compared to starting pH at t=0; and a concentration of tranexamic acid within ±10% of the starting concentration at t=0.

Clause 20. The pharmaceutical composition according to any one of clauses 1 to 18, wherein the composition when stored for 6 months at 40° C. at 75% RH is capable of maintaining: a pH within about +0.5 points compared to starting pH at t=0; and a concentration of tranexamic acid within #10% of the starting concentration at t=0.

Clause 21. The pharmaceutical composition according to any one of clauses 1 to 20, wherein the pharmaceutical composition is an intramuscular pharmaceutical composition.

Clause 22. Use of the pharmaceutical composition according to any one of clauses 1 to 21 for manufacture of a medicament for treating hemorrhage in a subject in need thereof.

Clause 23. A method of treating hemorrhage in a subject in need thereof, comprising parenterally administering an effective amount of the pharmaceutical composition according to any one of clauses 1 to 21.

Clause 24. The method according to clause 23, wherein the administering comprises intramuscular administration.

Clause 25. The method according to clause 23 or 24, wherein the subject exhibits onset of a tranexamic acid plasma concentration of at least about 15 ug/mL within about 7 minutes, or within about 10 minutes, following intramuscular administration of the composition comprising at least about 1.0 g of the tranexamic acid or a pharmaceutically acceptable salt thereof.

Clause 26. The method according to any one of clauses 23 to 25, wherein the subject exhibits a tranexamic acid plasma concentration of at least about 15 ug/mL for at least about 100 min, at least about 110 min, or at least about 120 min following intramuscular administration of the composition comprising at least about 1.0 g of the tranexamic acid or a pharmaceutically acceptable salt thereof.

Clause 27. The method according to any one of clauses 23 to 26, wherein the subject exhibits a tranexamic acid plasma Cmax of no more than about 40 ug/mL, or no more than about 37 ug/mL, following intramuscular administration of the composition comprising about 1.0 g of the tranexamic acid or a pharmaceutically acceptable salt thereof.

Clause 28. An auto-injector arrangement, comprising: an auto-injector comprising an injector body housing the pharmaceutical composition according to any one of clauses 1 to 21.

Clause 29. The auto-injector arrangement of clause 28, wherein the injector body comprises a first flexible primary container for storing the pharmaceutical composition, and optionally a second flexible primary container for storing the pharmaceutical composition or at least one additional active agent separate from the pharmaceutical composition.

Clause 30. The auto-injector arrangement according to clause 29, wherein the at least one additional active agent is selected from the group consisting of an anesthetic, analgesic, and antimicrobial agent.

Clause 31. The auto-injector arrangement according to any one of clauses 28 to 30, comprising a primary container in communication with an intramuscular injection needle, the primary container comprising at least about 2 mL, at least about 3 mL, at least about 4 mL, or at least about 5 mL dose of the pharmaceutical composition.

Clause 32. The auto-injector arrangement according to clause 31, comprising a plurality of primary containers and a plurality intramuscular injection needles in fluid communication with respective primary containers for administering the dose to form multiple depots in the muscle.

Clause 33. The auto-injector arrangement of clause 32, comprising a plurality of primary containers accumulatively comprising at least 2 mL, at least 3 mL, at least 4 mL, or at least 5 mL dose of the pharmaceutical composition.

Clause 34. The auto-injector arrangement of clause 32, wherein each primary container is in fluid communication with at least one intramuscular injection needle for administering the dose to form the plurality of depots in the muscle.

Clause 35. An auto-injector arrangement, comprising: an auto-injector comprising an injector body housing a ready-to-mix pharmaceutical composition comprising a therapeutically effective amount of tranexamic acid or a pharmaceutically acceptable salt thereof; and an aqueous diluent which when mixed with the ready-to-mix composition is capable of forming an injectable pharmaceutical composition according to any one of clauses 1 to 21.

Clause 36. The auto-injector arrangement of clause 35, wherein the injector body comprises a flexible primary container comprising a first compartment for storing the ready-to-mix pharmaceutical composition and a second compartment for storing the aqueous diluent separate from the ready-to-mix pharmaceutical composition, wherein the first and second compartment are separated by a frangible seal prior to mixing.

Clause 37. The auto-injector arrangement according to clause 35, wherein the injectable pharmaceutical composition has a pH of no more than pH 5.0, no more than pH 4.5, or no more than pH 4.0.

Clause 38. The auto-injector arrangement according to clause 36, wherein the primary container is in communication with an intramuscular injection needle, the primary container having a volume capacity capable of housing at least 2 mL, at least 3 mL, at least 4 mL, or at least 5 mL dose of the diluted injectable pharmaceutical composition.

Clause 39. The auto-injector arrangement according to clause 38, comprising a plurality of primary containers each in communication with a plurality of intramuscular injection needles for administering the diluted injectable pharmaceutical composition to form multiple depots in the muscle.

Clause 40. The auto-injector arrangement of clause 39, wherein the plurality of primary containers accumulatively comprises a volume capacity capable of housing at least 2 mL, at least 3 mL, at least 4 mL, or at least 5 mL dose of the diluted injectable pharmaceutical composition.

Clause 41. The auto-injector arrangement of clause 40, wherein each primary container is in fluid communication with at least one intramuscular injection needle for administering the dose of diluted injectable pharmaceutical composition to form the plurality of depots in the muscle.

Clause 42. A kit comprising a prefilled aseptic primary container comprising the pharmaceutical composition according to any one of clauses 1 to 21 or an auto-injector arrangement according to any one of clauses 28 to 41, and optionally a sheet of instructions.

What is claimed is:

1. A ready-to-use injectable pharmaceutical composition comprising from about 200 mg/mL to about 600 mg/ml of tranexamic acid or a pharmaceutically acceptable salt thereof, the composition having a pH in a range of from about pH 3.0 to about pH 5.0.

2. The pharmaceutical composition according to claim 1, having a pH in a range of from about pH 3.0 to about pH 4.5, or from about pH 3.0 to about pH 4.0.

3. The pharmaceutical composition according to claim 1, comprising about 300 mg/mL to about 550 mg/mL, about 400 mg/mL to about 550 mg/mL, about 450 mg/mL to about 550 mg/mL, about 475 mg/mL to about 525 mg/mL, or about 400 mg/mL, about 425 mg/mL, about 450 mg/mL, about 475 mg/mL, about 500 mg/mL, about 525 mg/mL, about 550 mg/mL, about 575 mg/mL, or about 600 mg/mL of the tranexamic acid or pharmaceutically acceptable salt thereof in solution.

4. The pharmaceutical composition according to claim 1, comprising 200 to 450 mg/ml of the tranexamic acid or pharmaceutically acceptable salt thereof in solution, the composition having a pH in a range of from about pH 3.0 to about pH 4.5.

5. The pharmaceutical composition according to claim 1, comprising 400 to 450 mg/ml of the tranexamic acid or pharmaceutically acceptable salt thereof in solution, the composition having a pH in a range of from about pH 3.0 to about pH 4.0.

6. The pharmaceutical composition according to claim 1, comprising 300 to 500 mg/ml of the tranexamic acid or pharmaceutically acceptable salt thereof in solution, the composition having a pH in a range of from about pH 3.0 to about pH 4.0.

7. The pharmaceutical composition according to claim 1, wherein the composition is an aqueous solution that requires no dilution before administration.

8. The pharmaceutical composition according to claim 1, comprising one or more additives selected from the group consisting of pH adjuster, tonicity agent, anesthetic, buffer, solvent, preservative, carrier, and colorant.

9. The pharmaceutical composition according to claim 8, wherein the pH adjuster is hydrochloric acid.

10. The pharmaceutical composition according to claim 1, wherein the pharmaceutical composition is an intramuscular pharmaceutical composition.

11. An auto-injector arrangement, comprising:
an auto-injector comprising an injector body housing the pharmaceutical composition according to claim 1.

12. A pharmaceutically acceptable container comprising the pharmaceutical composition according to claim 1.

13. The pharmaceutically acceptable container of claim 12, wherein the pharmaceutically acceptable container is a plastic or glass container.

14. The pharmaceutically acceptable container of claim 12, wherein the pharmaceutically acceptable container is selected from a pouch, cartridge, reservoir, bag, blister, sachet, vial, or syringe.

15. The pharmaceutically acceptable container of claim 12, wherein the pharmaceutically acceptable container is a pre-filled single dose dispensing device, or an aseptic container that may be transferred to a dispensing device shortly before use.

16. The pharmaceutically acceptable container of claim 12, wherein the pharmaceutically acceptable container is a pre-filled syringe.

17. The pharmaceutically acceptable container of claim 12, wherein the pharmaceutically acceptable container is a glass vial.

18. The pharmaceutically acceptable container of claim 12, wherein the pharmaceutically acceptable container is a USP Type I borosilicate glass vial or USP Type II soda lime silica glass vial.

19. The pharmaceutically acceptable container of claim 12, wherein the pharmaceutically acceptable container is a flexible primary container comprised within an injector body of an auto-injector arrangement.

20. The pharmaceutically acceptable container of claim 12, wherein the pharmaceutically acceptable container further comprises a light barrier to reduce the amount of light that reaches the pharmaceutical composition.

* * * * *